US010188824B2

(12) United States Patent
Gharazozloo et al.

(10) Patent No.: US 10,188,824 B2
(45) Date of Patent: Jan. 29, 2019

(54) AEROSTASIS IN PULMONARY SURGERY

(71) Applicant: ARIZONA BOARD OF REGENTS ON BEHALF OF THE UNIVERSITY OF ARIZONA, Tucson, AZ (US)

(72) Inventors: Farid Gharazozloo, Tucson, AZ (US); Barbara Tempesta, Tucson, AZ (US); Stephen H. Burke, Wixom, MI (US)

(73) Assignee: THE ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 307 days.

(21) Appl. No.: 14/891,162

(22) PCT Filed: May 13, 2014

(86) PCT No.: PCT/US2014/037908
§ 371 (c)(1),
(2) Date: Nov. 13, 2015

(87) PCT Pub. No.: WO2014/186401
PCT Pub. Date: Nov. 20, 2014

(65) Prior Publication Data
US 2016/0074617 A1    Mar. 17, 2016

Related U.S. Application Data

(60) Provisional application No. 61/822,831, filed on May 13, 2013.

(51) Int. Cl.
| | |
|---|---|
| *A61M 16/14* | (2006.01) |
| *A61M 11/00* | (2006.01) |
| *A61M 13/00* | (2006.01) |
| *A61M 16/00* | (2006.01) |

(Continued)

(52) U.S. Cl.
CPC ............ *A61M 16/14* (2013.01); *A61B 90/98* (2016.02); *A61M 11/005* (2013.01);
(Continued)

(58) Field of Classification Search
CPC ............... A61M 16/14; A61M 13/003; A61M 16/0051; A61M 11/005;
(Continued)

(56) References Cited

U.S. PATENT DOCUMENTS

| | | | |
|---|---|---|---|
| 6,015,100 A * | 1/2000 | Restive | .................. B05B 7/005 239/428.5 |
| 6,063,055 A | 5/2000 | Epstein et al. | |

(Continued)

OTHER PUBLICATIONS

International Search Report and Written Opinion for PCT/US2014/037908.

*Primary Examiner* — Bhisma Mehta
*Assistant Examiner* — Hamza Darb
(74) *Attorney, Agent, or Firm* — Gavin J. Milczarek-Desai; Quarles & Brady LLP

(57) ABSTRACT

A device for use in pulmonary surgery is presented. The device includes a dispensing apparatus 300, 400, 900, a delivery apparatus 100, 1000, 1100, in fluid communication with said dispensing apparatus, and a pressurized gas input 338. The dispensing apparatus is configured to provide a pressurized gas, a fibrinogen stream, and a thrombin stream to the delivery apparatus. The delivery apparatus is configured to mix the fibrogen stream and the thrombin stream in the pressurized gas stream to form a fibrin reaction mixture comprising a cellular foam 700.

10 Claims, 22 Drawing Sheets

(51) Int. Cl.
*A61B 90/98* (2016.01)
*A61M 16/04* (2006.01)

(52) U.S. Cl.
CPC ...... *A61M 13/003* (2013.01); *A61M 16/0051* (2013.01); *A61M 16/0406* (2014.02); *A61M 2202/0208* (2013.01); *A61M 2202/0427* (2013.01); *A61M 2205/3344* (2013.01); *A61M 2205/3368* (2013.01); *A61M 2205/3653* (2013.01); *A61M 2205/502* (2013.01); *A61M 2205/8206* (2013.01)

(58) Field of Classification Search
CPC ...... A61M 2205/3368; A61M 16/0406; A61M 2202/0427; A61M 2202/0208; A61M 2205/3653; A61M 2205/502; A61M 2205/8206; A61M 2205/3344
See application file for complete search history.

(56) References Cited

U.S. PATENT DOCUMENTS

| | | | |
|---|---|---|---|
| 6,113,571 A | 9/2000 | Zinger et al. | |
| 6,319,458 B1* | 11/2001 | Jung | C21B 5/003 266/266 |
| 2003/0187408 A1* | 10/2003 | Marx | A61B 17/00491 604/236 |
| 2005/0241605 A1* | 11/2005 | Bedwell | F02M 29/14 123/184.21 |
| 2008/0121046 A1 | 5/2008 | Glezer et al. | |
| 2010/0028236 A1 | 2/2010 | Shen et al. | |
| 2010/0331766 A1* | 12/2010 | Hayakawa | A61B 17/00491 604/24 |
| 2014/0271897 A1* | 9/2014 | Pathak | A61K 9/5031 424/497 |

* cited by examiner

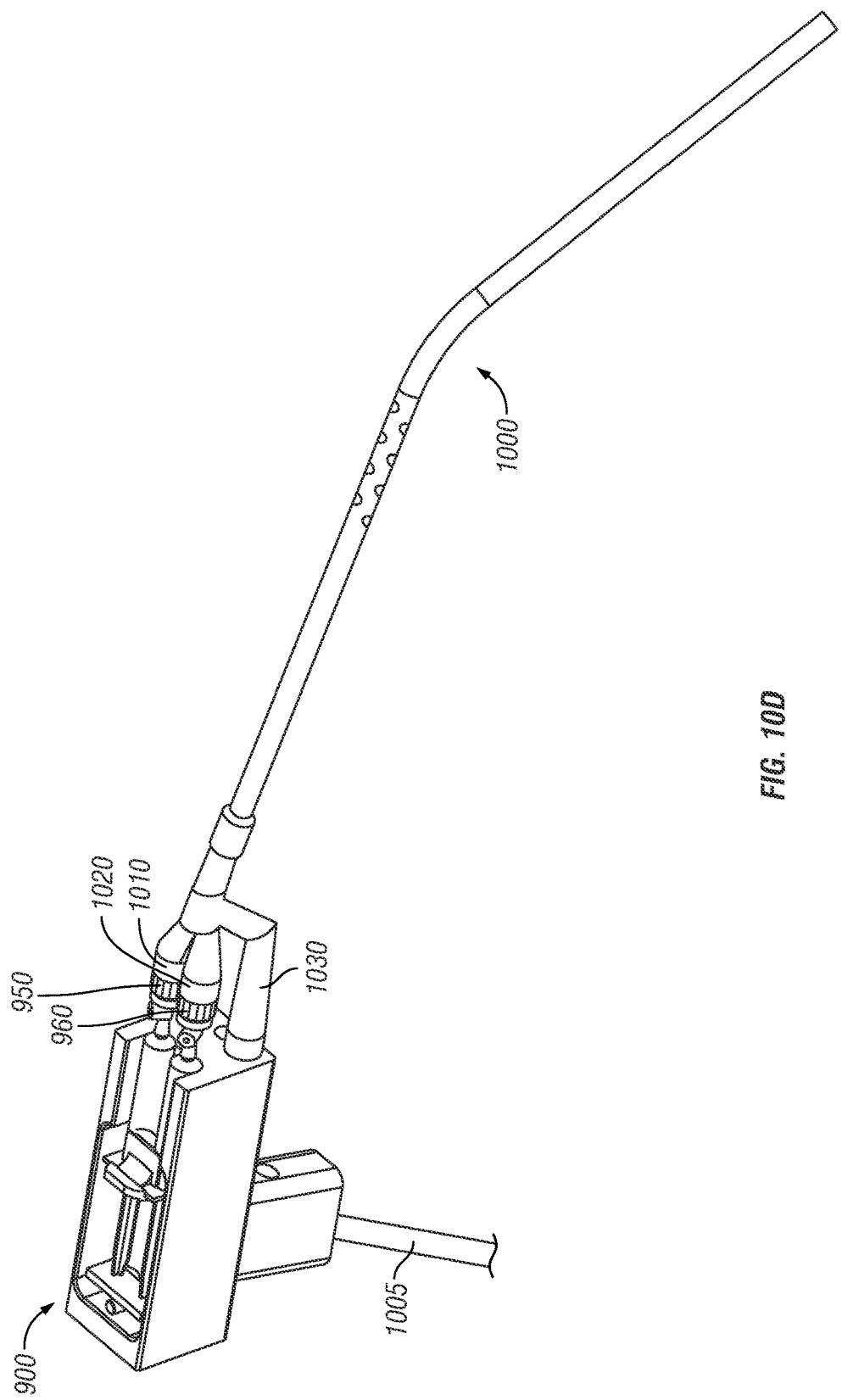

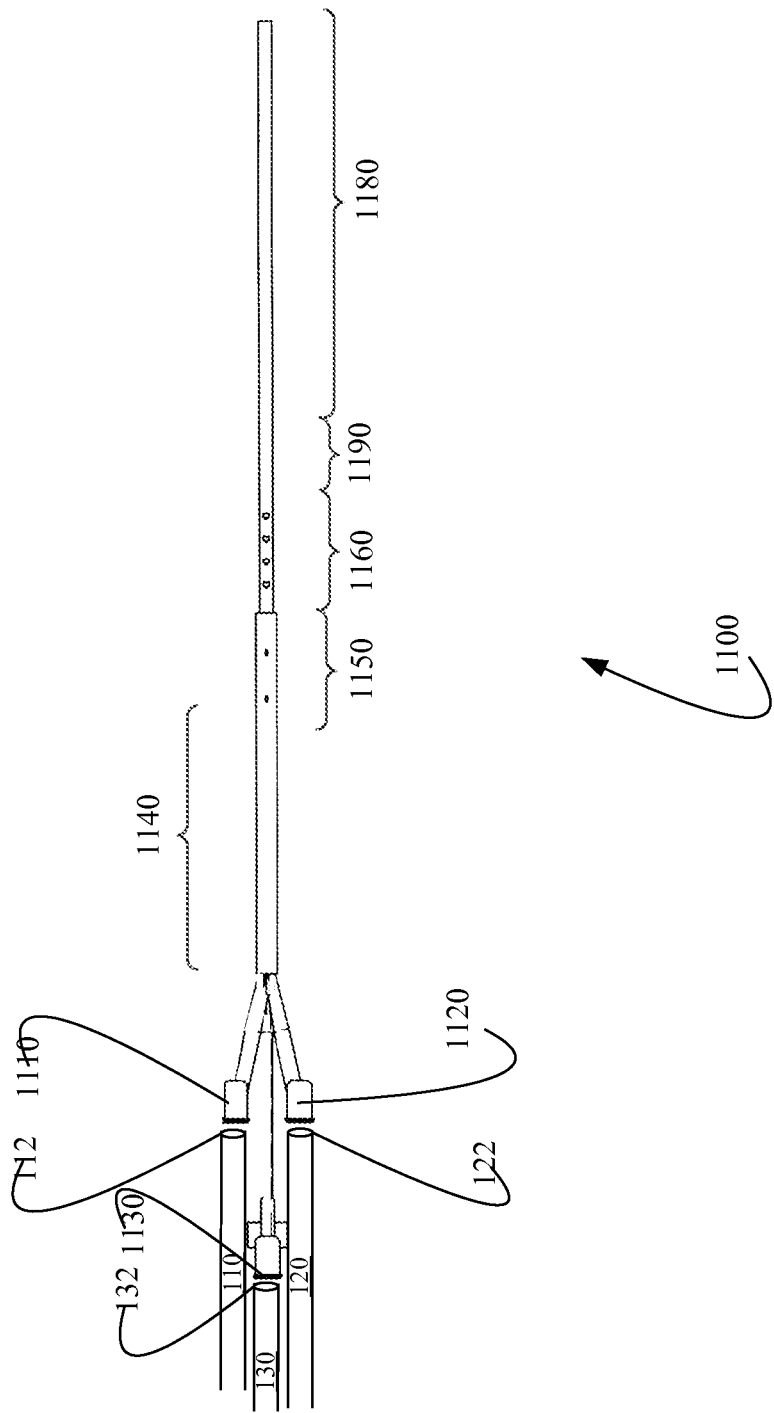

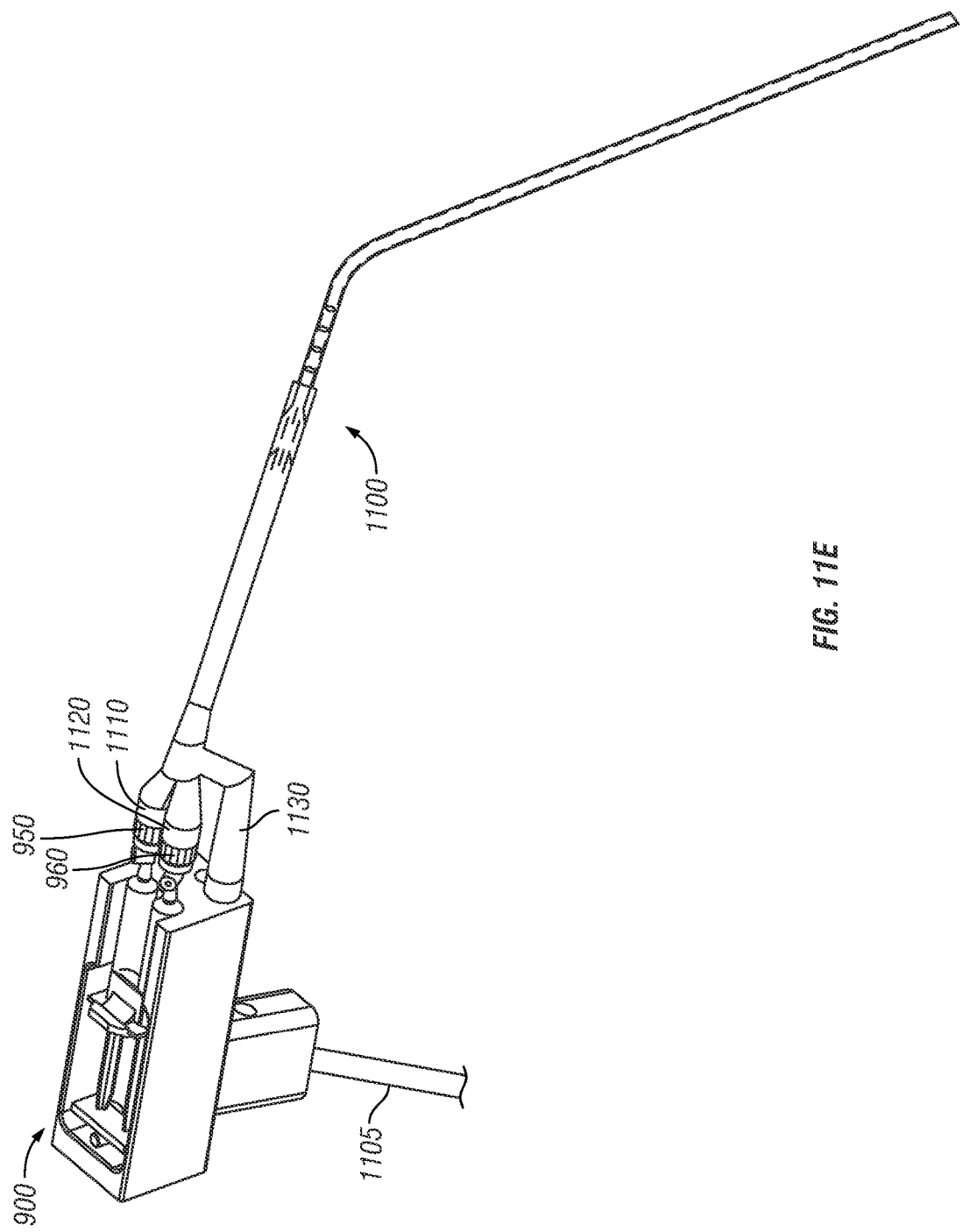

AEROSTASIS IN PULMONARY SURGERY

CROSS-REFERENCE TO RELATED APPLICATIONS

This application claims benefit of priority under 35 U.S.C. 119(e) to International Application No. PCT/US2014/037908 filed on May 13, 2014, the entire contents of which are incorporated herein by reference.

FIELD OF THE INVENTION

The invention is directed to an device and method for aerostasis in pulmonary surgery.

BACKGROUND OF THE INVENTION

About fifty thousand (50,000) pulmonary surgical procedures are performed annually. At least twenty-five percent (25%) of these patients experience air leaks after surgery. Such air leaks prevent full pulmonary function. Moreover, such air leaks are the most common cause of delayed discharge. The discharge of about fifteen percent (15%) of pulmonary surgery patients is delayed at least 7 days.

A study of 319 patients from January, 1998 to July 2001 experienced air leaks in fifty-eight percent (58%). About fifty percent of these patients experienced air leaks 3 days after surgery.

Risk factors for prolonged hospitalization include increased age, smoking, use of steroids, and use of chemo/radiation therapy. Underlying pulmonary diseases include chronic obstructive pulmonary disease, tuberculosis, bullous disease, and pulmonary fibrosis. As a general matter, air leaks cause increased morbidity, increased infection, increased rate of BP fistula, increased hospitalization, and increased cost.

SUMMARY OF THE INVENTION

A device for use in pulmonary surgery is presented. The device comprises a dispensing apparatus, a delivery apparatus in fluid communication with said dispensing apparatus, and a pressurized gas input. The dispensing apparatus is configured to provide a pressurized gas, a fibrinogen stream, and a thrombin stream to the delivery apparatus. The delivery apparatus is configured to mix the fibrogen stream and the thrombin stream in the pressurized gas stream to form a fibrin reaction mixture comprising a cellular foam.

A method for preventing air leaks from a serosal tissue wound is presented. The method includes providing a device comprising a dispensing apparatus and a delivery apparatus in fluid communication with the dispensing apparatus. The method further includes rapidly warming frozen aliquots of fibrinogen and thrombin from about 0° C. to about 37° C. in about 3 minutes or less, and providing within about 5 minutes after completion of said rapidly warming the about 37° C. fibrinogen aliquot and the about 37° C. thrombin aliquot from the dispensing apparatus to the delivery apparatus.

The method then mixes a fibrogen stream and a thrombin stream in a pressurized gas stream, where that pressurized gas stream has a pressure of 50 psi or greater. The method generates a fibrin-forming foam, and directs that fibrin-forming foam onto the serosal tissue wound.

BRIEF DESCRIPTION OF THE DRAWINGS

The invention will be better understood from a reading of the following detailed description taken in conjunction with the drawings in which like reference designators are used to designate like elements, and in which:

FIG. 10D illustrates application apparatus 1000 directly coupled to dispensing apparatus 900;

FIG. 11A illustrates a fourth embodiment of Applicants' application apparatus;

FIG. 11E illustrates application apparatus 1100 directly coupled to dispensing apparatus 900.

DETAILED DESCRIPTION OF PREFERRED EMBODIMENTS

This invention is described in preferred embodiments in the following description with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow charts included are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Applicants' device and method using that device results in pulmonary aerostasis, i.e. a decreased rate of air leaks. As a result, patients experience increased comfort and satisfaction, decreased complications, decreased use of analgesics, decreased hospitalization, and decreased costs.

Applicants' device comprises a dispensing apparatus and an application apparatus. Referring to FIGS. 1A, 1B, 2A, 2B, and 3A, in certain embodiments Applicants' device comprises dispensing apparatus 300 and application apparatus 100.

Figure 1A:
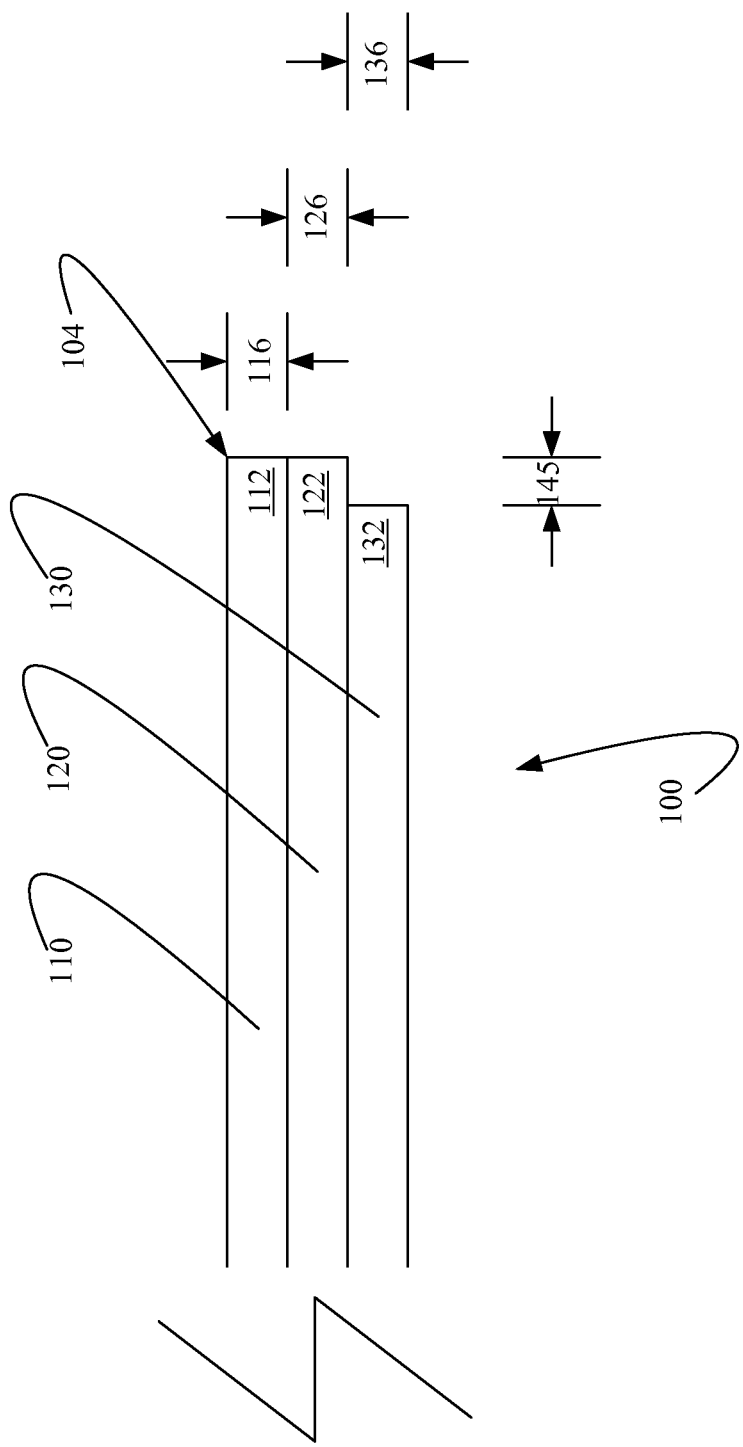
FIG. 1A illustrates a first embodiment of a distal end of Applicants' application apparatus.
Figure 1B:
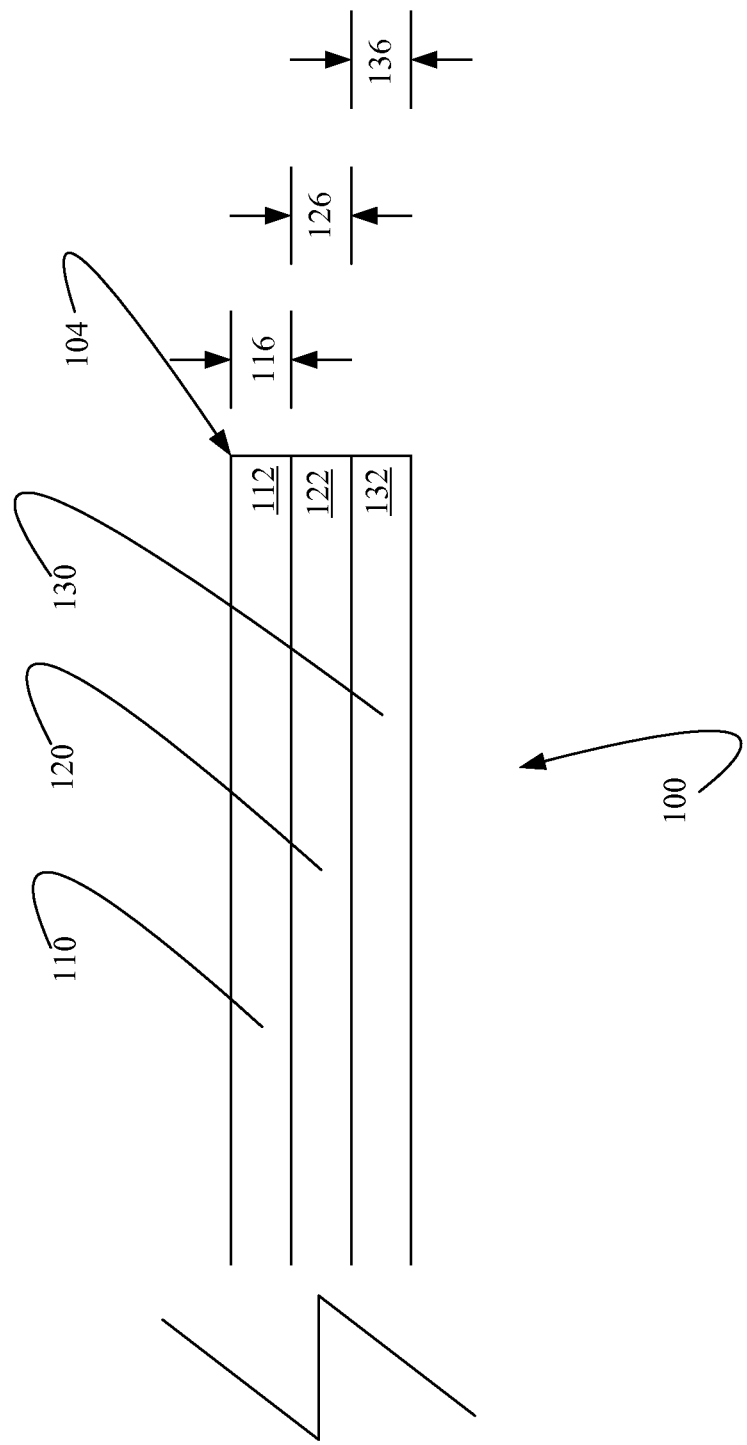
FIG. 1B illustrates a second embodiment of a distal end of Applicants' application apparatus.

Application apparatus 100 comprises a first end 102 (FIG. 3) and a second end 104 (FIG. 1). In the illustrated embodiment of FIGS. 1A, 1B, 2A, and 2B, application apparatus 100 comprises three catheters, including catheters 110, 120, and 130.

In the illustrated embodiment of FIG. 1A, end 132 of catheter 130 is offset from ends 112 of catheter 110 and 122 of catheter 120 by an offset distance 145. In certain embodiments, offset distance 145 is between about 1 mm and about 10 mm. In certain embodiments offset distance 145 is about 5 mm.

In certain embodiments, catheter 110 is formed from one or more elastomer. In certain embodiments, catheter 110 is formed from one or more sterilizable elastomers. In certain embodiments, catheter 110 comprises an elastomer selected from the group comprising polytetrafluoroethylene, polyurethane, silicone, latex, and combinations thereof.

Figure 2A:
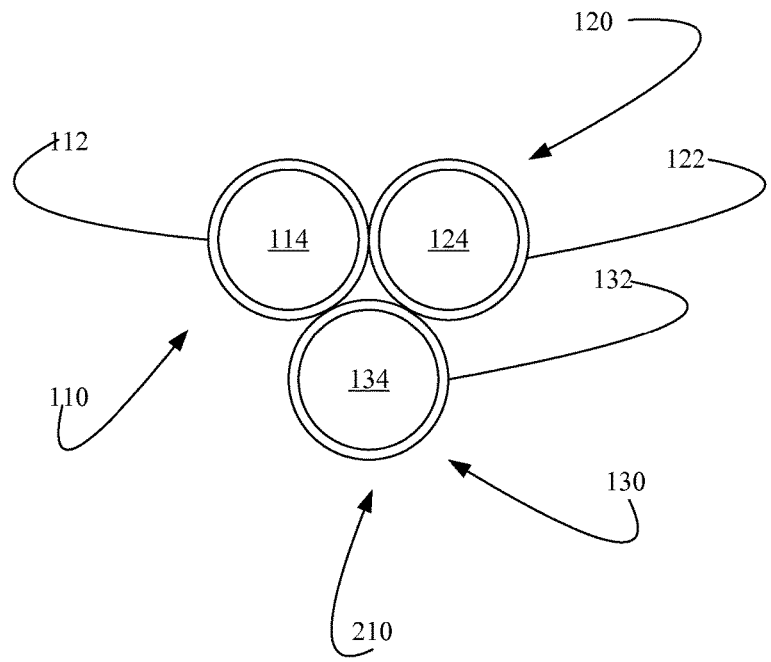
FIG. 2A illustrates a first structure for a distal end of Applicants' application apparatus.
Figure 2B:
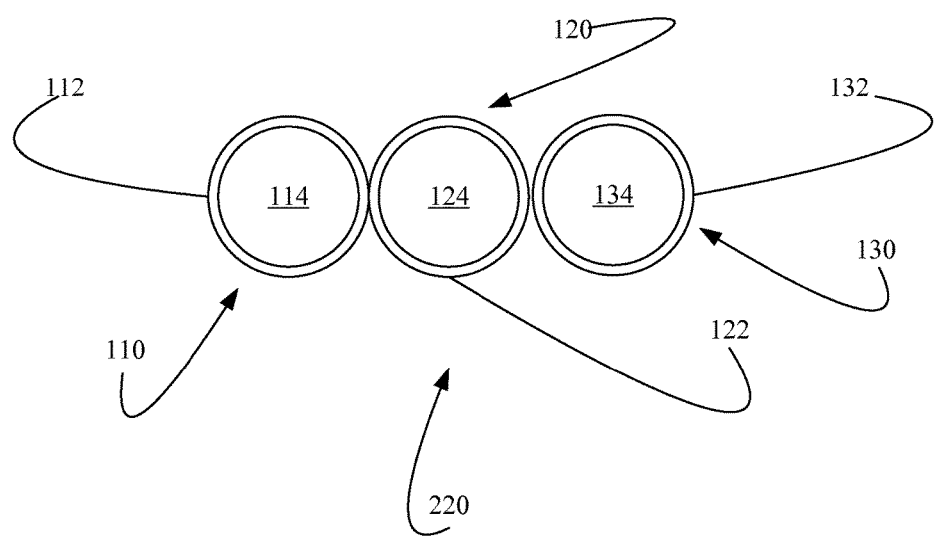
FIG. 2B illustrates a second structure for a distal end of Applicants' application apparatus.

Referring now to FIGS. 1, 2A, and 2B, open end 112 of catheter 110 is formed to include an aperture 114 therein, wherein aperture 114 is formed to comprise a diameter 116. In certain embodiments, diameter 116 is between about 0.10 mm and about 2.0 mm. In certain embodiments, diameter 116 is about 0.5 mm.

In certain embodiments, catheter 120 is formed from one or more elastomers. In certain embodiments, catheter 120 is formed from one or more sterilizable elastomers. In certain embodiments, catheter 120 comprises an elastomer selected from the group comprising polytetrafluoroethylene, polyurethane, silicone, latex, and combinations thereof.

Open end 122 of catheter 120 is formed to include an aperture 124 therein, wherein aperture 124 is formed to comprise a diameter 116. In certain embodiments, diameter 126 is between about 0.10 mm and about 2.0 mm. In certain embodiments, diameter 126 is about 0.5 mm.

In certain embodiments, catheter 130 is formed from one or more elastomers. In certain embodiments, catheter 130 is formed from one or more sterilizable elastomers. In certain embodiments, catheter 130 comprises an elastomer selected from the group comprising polytetrafluoroethylene, polyurethane, silicone, latex, and combinations thereof.

Open end 132 of catheter 130 is formed to include an aperture 134 therein, wherein aperture 134 is formed to comprise a diameter 136. In certain embodiments, diameter 136 is between about 1 mm and about 5 mm. In certain embodiments, diameter 136 is about 2 mm.

In certain embodiments second end 104 of application apparatus 100 comprises architecture 210. In certain embodiments second end 104 of application apparatus 100 comprises architecture 210 wherein end 132 of catheter 130 is offset from ends 112 of catheter 110 and 122 of catheter 120 by offset distance 145.

In certain embodiments second end 104 of application apparatus 100 comprises architecture 220. In certain embodiments second end 104 of application apparatus 100 comprises architecture 220 wherein end 132 of catheter 130 is offset from ends 112 of catheter 110 and 122 of catheter 120 by offset distance 145.

Referring once again to FIG. 3A, first end 102 of application apparatus 100 is in fluid communication with fluid interface 360. Fluid interface 360 is further in fluid communication with conduits 318, 328, and 338. Conduit 318 is in fluid communication with first reservoir 310 via outlet 316. Conduit 328 is in fluid communication with second reservoir 320 via outlet 326. Conduit 338 is in fluid communication with valve 350.

In certain embodiments, catheter 110 and fluid conduit 318 comprise an integral structure. In certain embodiments, catheter 120 and fluid conduit 328 comprise an integral structure and do not include fluid interface 336.

In certain embodiments, first reservoir 310 comprises a cylindrical shape. In certain embodiments, piston 312 comprises a circular cross-section and is slideably disposed within first reservoir 310.

In certain embodiments, second reservoir 320 comprises a cylindrical shape. In certain embodiments, piston 332 comprises a circular cross-section and is slideably disposed within second reservoir 320.

Figure 3A:
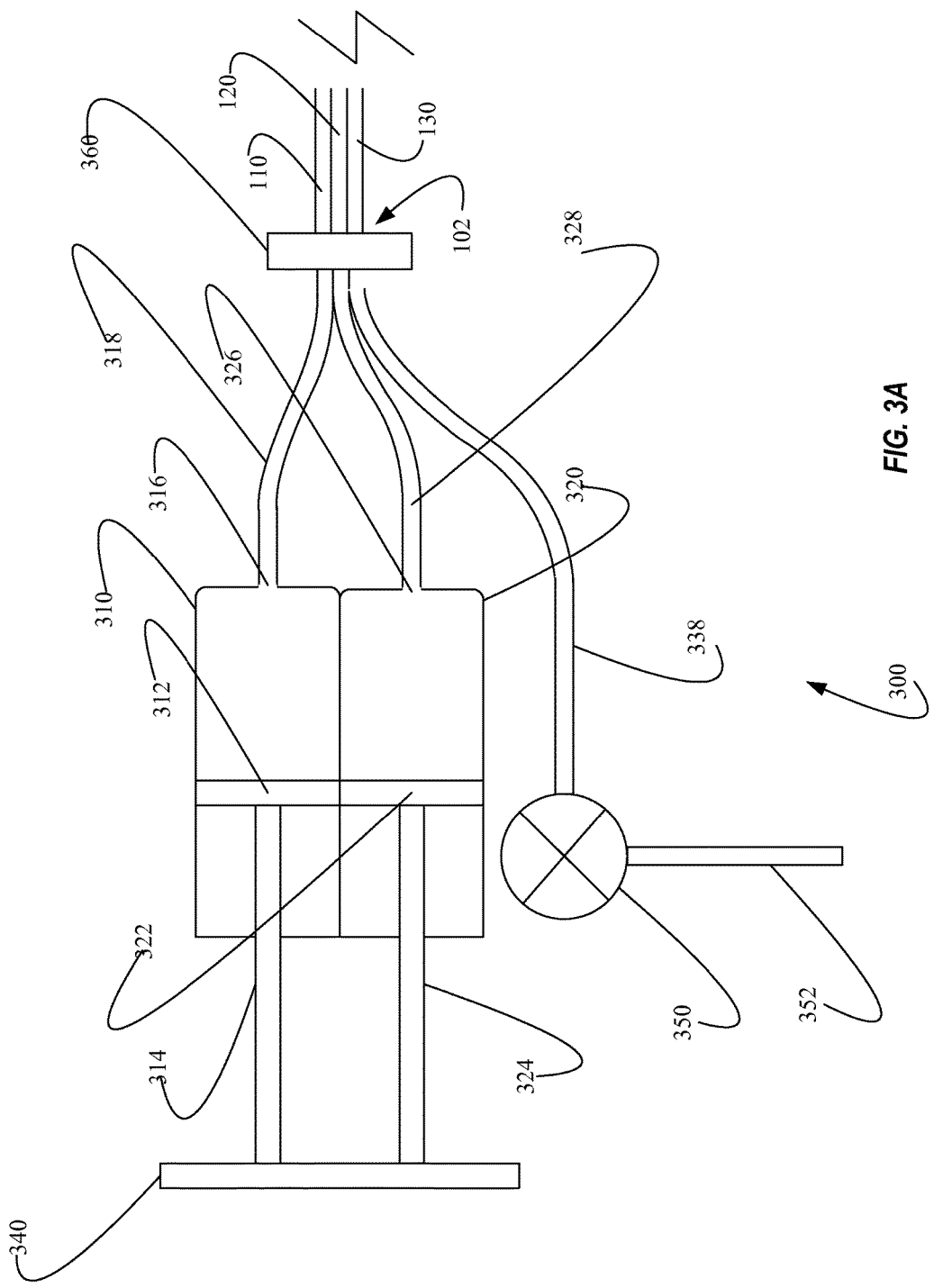
FIG. 3A illustrates a first embodiment of Applicants' dispensing apparatus.

In the illustrated embodiment of FIG. 3A a first end of connecting member 314 is attached to piston 312 and a second end of connecting member 314 extends outwardly from first reservoir 310. In the illustrated embodiment of FIG. 3 a first end of connecting member 324 is attached to piston 322 and a second end of connecting member 324 extends outwardly from second reservoir 320.

In the illustrated embodiment of FIG. 3A, activation member 340 is attached to both connecting member 314 and connecting member 324. Moving activation member 340 toward reservoir 310 causes piston 312 to move toward outlet 316 thereby forcing a fluid from reservoir 310 through conduit 316, through catheter 110, and out of aperture 114. Similarly, moving activation member 340 toward reservoir 320 causes piston 322 to move toward outlet 326 thereby forcing a fluid from reservoir 320, through conduit 326, through catheter 120, and out of aperture 124.

In the illustrated embodiment of FIG. 3A, moving activation member 340 causes movement of piston 312 and piston 322. Use of a single activation member facilitates one-hand operation of dispensing apparatus 300.

Figure 3B:
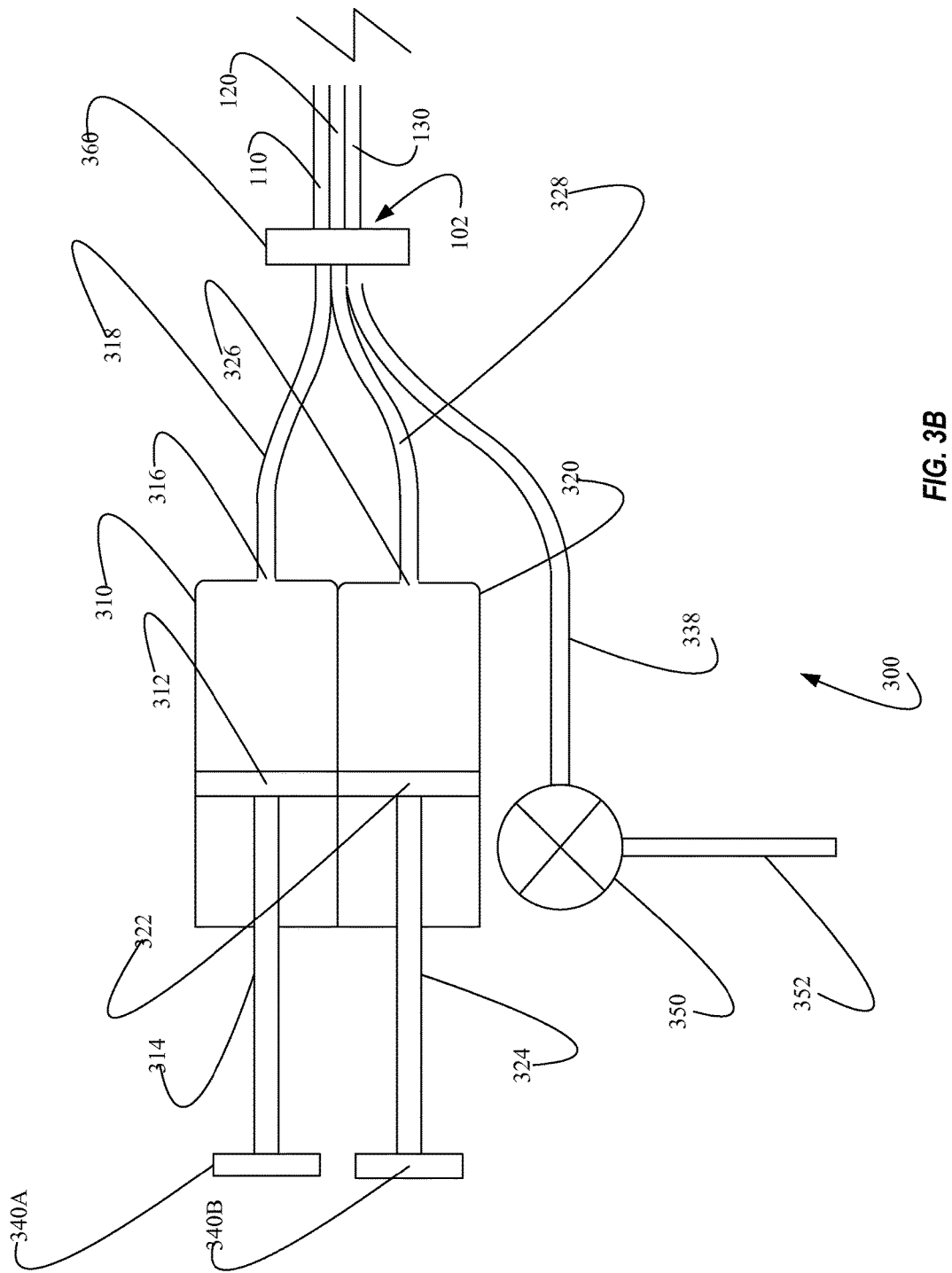
FIG. 3B illustrates a second embodiment of Applicants' dispensing apparatus.

Referring now to FIG. 3B, a first activation member 340A is attached to connecting member 314 but not to connecting member 324. Moving activation member 340A causes movement of piston 312 but not piston 314. In these embodiments, a second activation member 340B is attached to connecting member 324 but not to connecting member 314. Moving activation member 340B causes movement of piston 314 but not piston 312.

In certain embodiments, reservoir 310, and/or connecting member 314, and/or activation member 340, are is molded from one or more rigid polymeric materials. In certain embodiments, reservoir 310, and/or connecting member 314, and/or activation member 340, are formed from one or more metals. In certain embodiments, reservoir 320 and/or connecting member 324 are molded from one or more polymeric materials. In certain embodiments, reservoir 320 and/or connecting member 324 are formed from one or more metals.

In certain embodiments, reservoir 310 and reservoir 320 are formed from glass. In certain embodiments, reservoir 310 and reservoir 320 comprise a unitary structure.

Valve 350 interconnects conduit 338 to a source of pressurized gas 352. In certain embodiments, the pressurized gas comprises sterile oxygen. In certain embodiments, the pressurized gas comprises sterile air.

Figure 4:
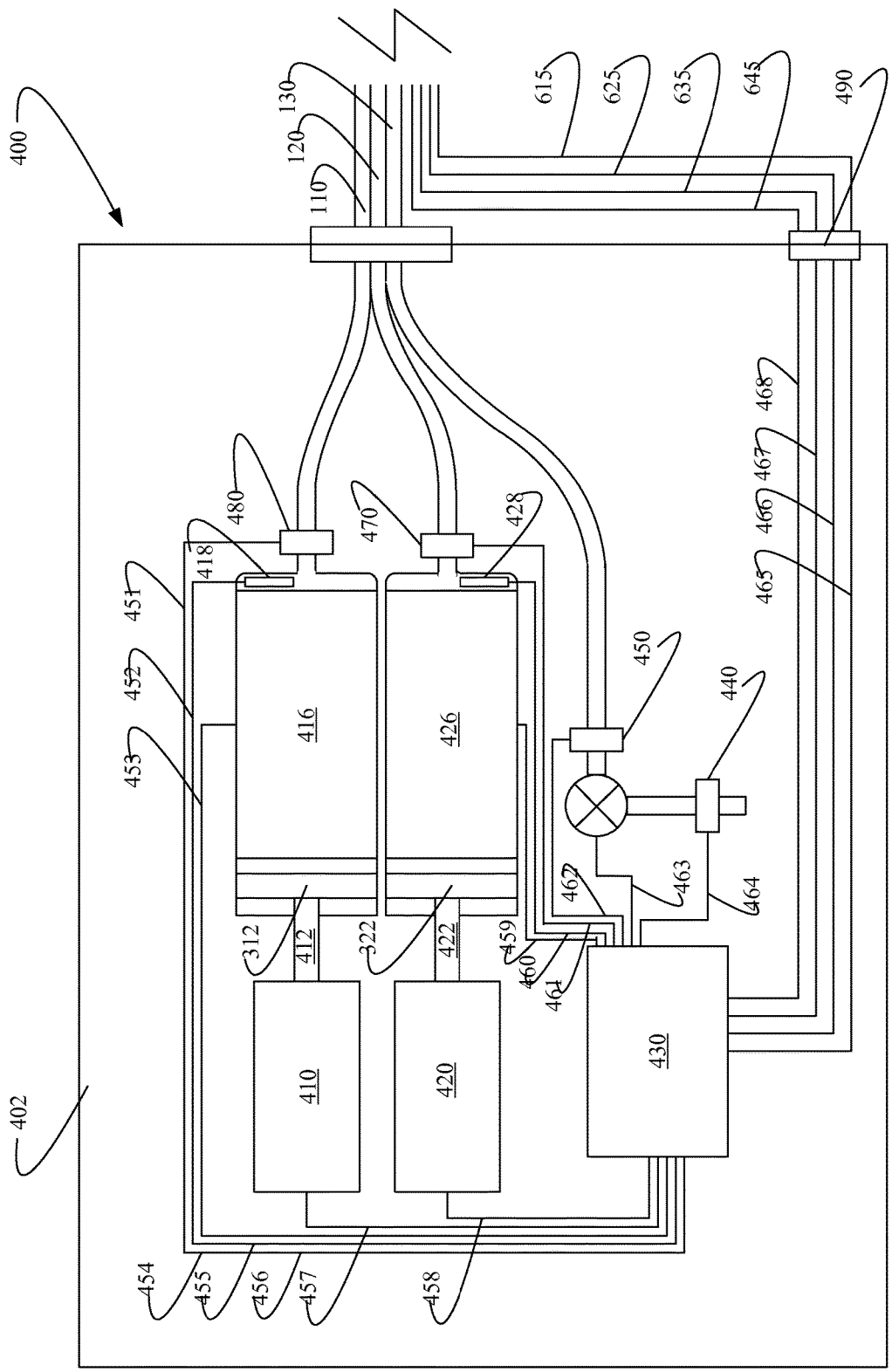
FIG. 4 illustrates a third embodiment of Applicants' dispensing apparatus comprising a controller.

FIG. 4 illustrates dispensing apparatus 400. Dispensing apparatus 400 comprises first reservoir 310 (FIGS. 3A, 3B), piston 312 (FIGS. 3A, 3B), second reservoir 320 (FIGS. 3A, 3B), piston 322 (FIGS. 3A, 3B), valve 350 (FIGS. 3A, 3B), and conduits 318 (FIGS. 3A, 3B), 328 (FIGS. 3A, 3B), and 338 (FIGS. 3A, 3B). In addition, dispensing apparatus comprises solenoid 410, wherein solenoid 410 can cause armature 412 to move inwardly and outwardly from solenoid 410. Armature 412 is interconnected to piston 312. Solenoid 410 is in communication with controller 430 via communication link 457.

Solenoid 420 can cause armature 422 to move inwardly and outwardly from solenoid 420. Armature 422 is interconnected to piston 322. Solenoid 420 is in communication with controller 430 via communication link 458.

References herein to a solenoid device should not be taken as limiting. In certain embodiments, devices 410 and 420 comprise any electromechanical assemblies that can cause armatures 412 and 422, respectively, to move inwardly into and/or outwardly therefrom.

Heating element 416 is disposed around first reservoir 310. Heating element is in communication with controller 430 via communication link 453. Temperature sensor 418 is disposed on the outer surface of first reservoir 310. Temperature sensor is in communication with controller 430 via communication link 452. Pressure transducer 480 monitors the pressure within conduit 318. Pressure transducer 480 is in communication with controller 430 via communication link 451.

Heating element 426 is disposed around second reservoir 320. Heating apparatus 426 is in communication with controller 430 via communication link 459. Temperature sensor 428 is disposed on the outer surface of second reservoir 320. Temperature sensor 428 is in communication with controller 430 via communication link 460. Pressure transducer 470 monitors the pressure within conduit 318. Pressure transducer 470 is in communication with controller 430 via communication link 461.

Pressure transducer 440 monitors the pressure in pressurized gas source line 352. Pressure transducer 440 is in communication with controller 430 via communication link 464. Pressure transducer 450 monitors the pressure in gas conduit 338. Pressure transducer 450 is in communication with controller 430 via communication link 462.

As those skilled in the art will appreciate, FIG. 4 does not show power distribution within dispensing apparatus 400. In certain embodiments, devices 350, 410, 416, 418, 420, 426,428, 430, 440, 450, 470, 480, and 490, received power from a power source internal to housing 402, i.e. one or more batteries. In other embodiments, devices 350, 410, 416, 418, 420, 426,428, 430, 440, 450, 470, 480, and 490, received power from a power source external to housing 402, i.e. utility power.

Figure 9A:
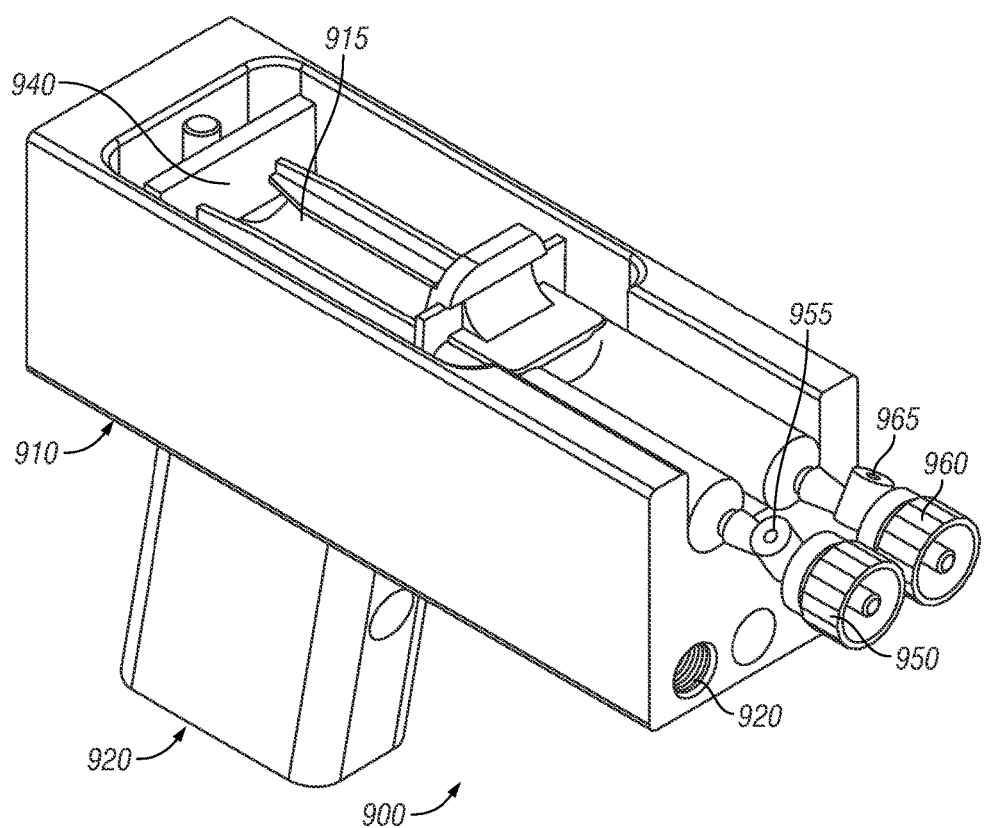
FIG. 9A is a perspective view of a third embodiment of Applicants' dispensing apparatus.

Referring now to FIG. 9A, dispensing apparatus 900 comprises a housing 910 and a handle 920. Housing 910 is formed to include a component bay 915. Pneumatic plunger 940 is moveably disposed within component bay 915. Housing 910 is further formed to include a threaded input port 920.

Housing 910 is further formed to include output ports 950 and 960. In certain embodiments, output ports 950 and 960 are configured to couple to proximal ends of catheters 110 and 120. In other embodiments, output ports 950 and 960 are configured to couple to input ports 1010 (FIG. 10A) and 1020 (FIG. 10A) of delivery apparatus 1000 (FIGS. 10A, 10B, 10C, 10D). In yet other embodiments, output ports 950 and 960 are configured to couple to input ports 1110 (FIG. 11A) and 1120 (FIG. 11A) of delivery apparatus 1100 (FIGS. 11A, 11B, 11C, 11D, 11E).

Figure 9B:
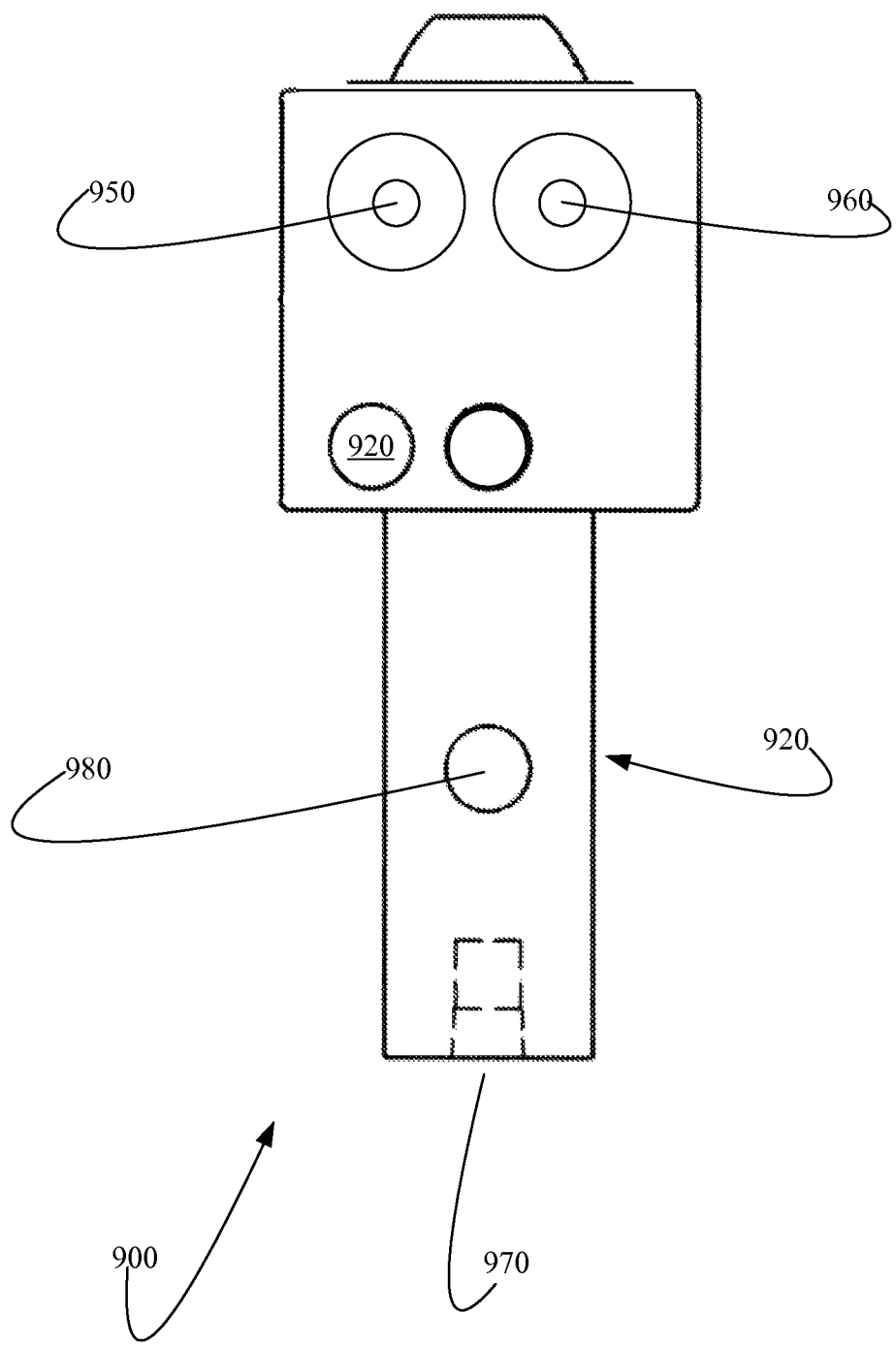
FIG. 9B is a front view of the dispensing apparatus of FIG. 9A.

Referring now to FIG. 9B, compressed gas input 970 is configured to couple to a source of pressurized gas. Activating button 980 is moveably disposed on handle 920 of dispensing apparatus 900.

Figure 9C:
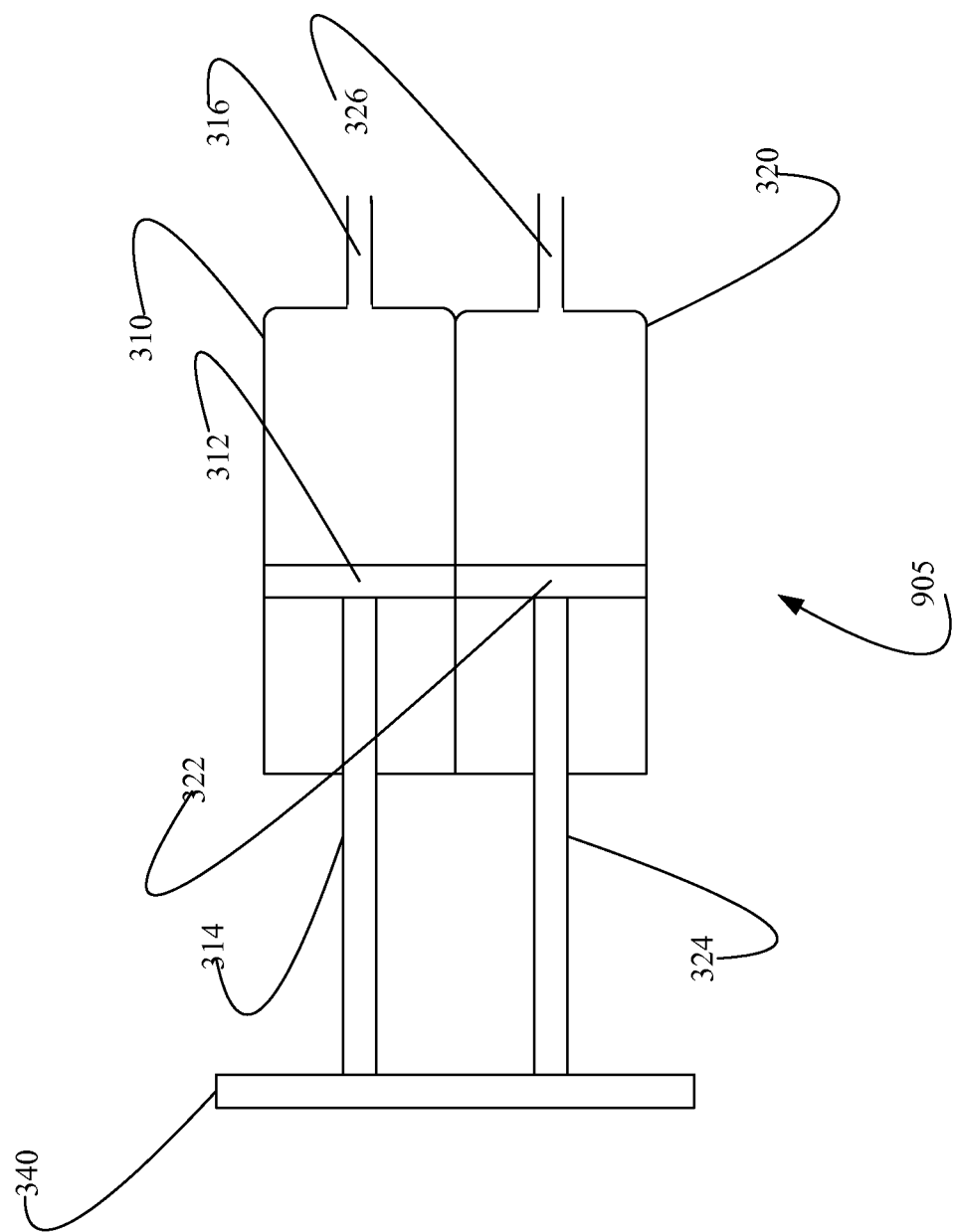
FIG. 9C illustrates a sub-assembly configured to be removeably disposed within the dispensing apparatus of FIG. 9A.

Referring now to FIG. 9C, in certain embodiments assembly 905 comprises a subassembly of dispensing apparatus 300 (FIG. 3A). In other embodiments, assembly 905 comprises an EVICEL applicator sold in commerce by JOHNSON & JOHNSON.

When dispensing fibrinogen and thrombin from dispensing apparatus 900, in certain embodiments subassembly 905 is removeably disposed within component bay 915 of dispensing apparatus 900 such that plunger 340 is disposed adjacent to reservoirs 310 and 320. In certain embodiments, activation member 340 is attached to pneumatic plunger 940. A source of pressurized gas is coupled to input port 970.

An ampoule of room temperature fibrinogen is coupled to input port 955. An ampoule of room temperature thrombin is coupled to input port 965. In certain embodiments, activation member 340 is manually moved outwardly to draw the fibrinogen and thrombin into reservoirs 320 and 310, respectively. In other embodiments, pneumatic plunger 940 is coupled to activation member 340, and pneumatic plunger 940 is caused to move backwardly to draw the fibrinogen and thrombin into reservoirs 320 and 310, respectively.

Depressing activation button 980 activates two air switches sequentially. In this two step process, compressed gas lines within dispensing apparatus 900 and within an attached delivery apparatus are first filled with pressurized gas, and then pneumatic plunger 940 is caused to rapidly move activation member 340 forward thereby causing pistons 312 and 322 to rapidly expel thrombin and fibrinogen outwardly from reservoirs 310 and 320, respectively.

Figure 6:
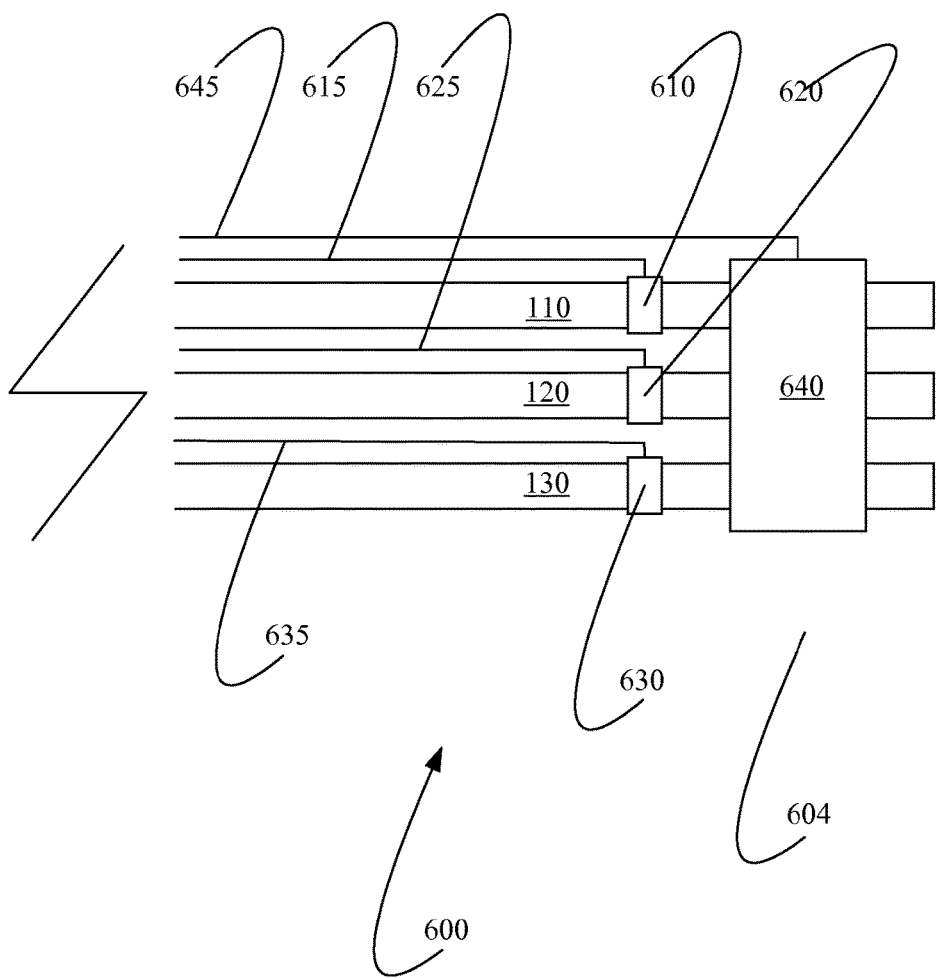
FIG. 6 illustrates a third embodiment of a distal end of Applicants' application apparatus.

Referring now to FIGS. 4 and 6, in certain embodiments, Applicants' application apparatus comprises pressure transducer 610 on catheter 110 at second end 604 of application apparatus 600. Pressure transducer 610 is in communication with controller 430 via communication link 615. Communication link 615 interconnects with communication link 465 via communication link interface 490.

In certain embodiments, Applicants' application apparatus comprises pressure transducer 620 on catheter 120 at second end 604 of application apparatus 600. Pressure transducer 620 is in communication with controller 430 via communication link 625. Communication link 625 interconnects with communication link 466 via communication link interface 490.

in certain embodiments, Applicants' application apparatus comprises pressure transducer 630 on catheter 130 at second end 604 of application apparatus 600. Pressure transducer 630 is in communication with controller 430 via communication link 635. Communication link 635 interconnects with communication link 467 via communication link interface 490.

In the illustrated embodiment of FIG. 6, piezoelectric vibration generator 640 is disposed around catheters 110, 120, and 130. Piezoelectric vibration generator 640 is in communication with controller 430 via communication link 645. Communication link 645 interconnects with communication link 468 via communication link interface 490.

In certain embodiments, piezoelectric vibration generator 640 causes end 604 of application apparatus 600 to vibrate at a frequency of between about 1 Hertz and about 100 Hertz. In certain embodiments, piezoelectric vibration generator 640 utilizes the expansion/contraction properties of piezoelectric crystals for sonic and ultrasonic structural excitation of end 604. In certain embodiments, piezoelectric vibration generator 640 generates dynamic forces to very high frequencies.

Figure 5:
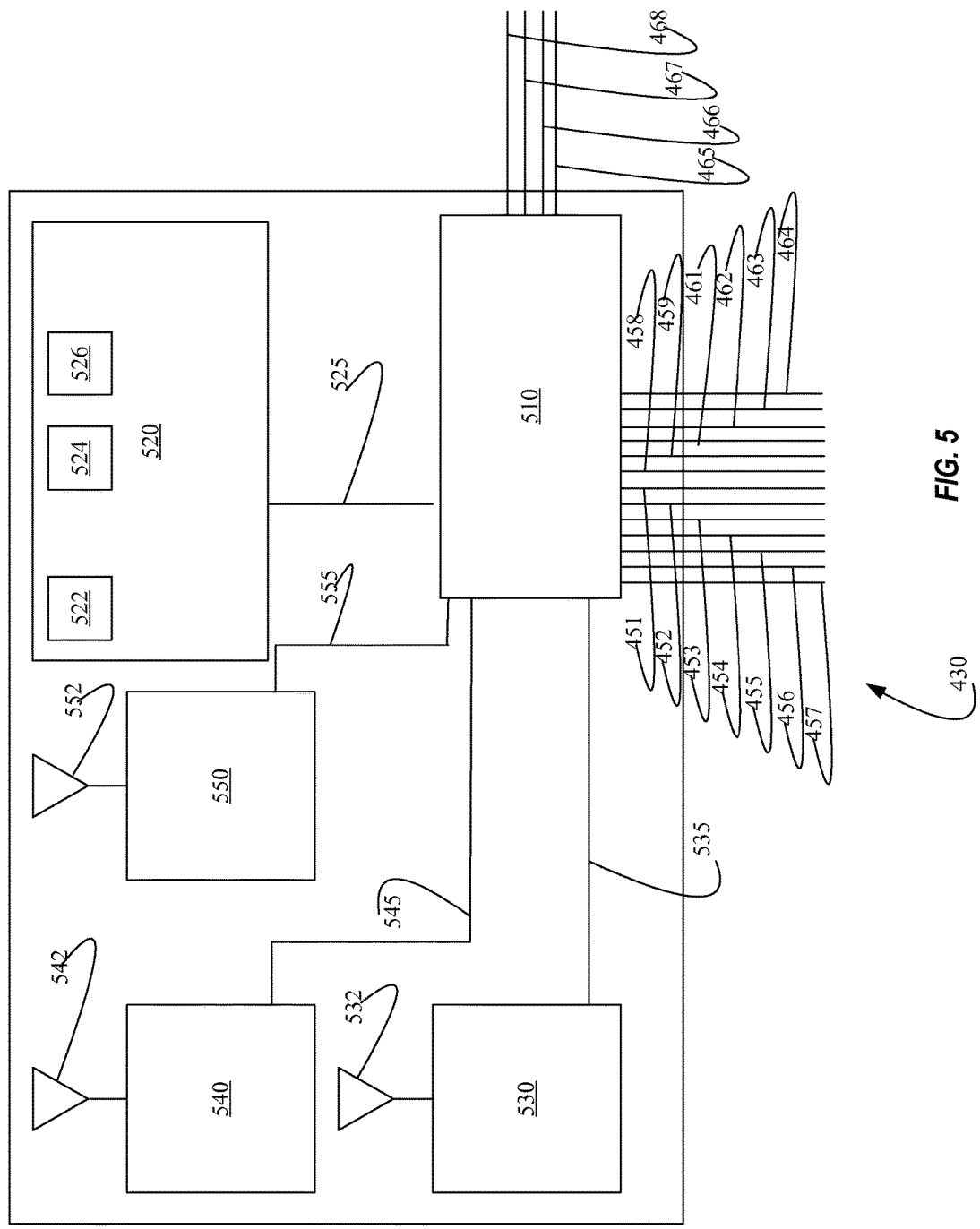
FIG. 5 illustrates an embodiment of the controller of FIG. 5.

Referring now to FIG. 5, controller 430 comprises processor 510, memory 520 interconnected with processor 510 via communication link 525, optional Blue Tooth module 530 interconnected with processor 510 via communication link 535, optional RFID module 540 interconnected with processor 510 via communication link 545, and optional "WI-FI" module 550 interconnected with processor 510 via communication link 555. In certain embodiments, controller 430 is disposed within dispensing device 900.

In the illustrated embodiment of FIG. 5, microcode 522, instructions 524, and database 526, are encoded in memory 520. In certain embodiments, memory 520 comprises non-volatile memory. In certain embodiments, memory 520 comprises battery backed up RAM, a magnetic hard disk assembly, an optical disk assembly, and/or electronic memory. By "electronic memory," Applicants mean a PROM, EPROM, EEPROM, SMARTMEDIA, FLASFIMEDIA, and the like.

Processor 510 uses microcode 522 to operate controller 430. Processor 510 uses microcode 522, instructions 524, and database 526, to operate Blue Tooth module 530, RFID module 540, WI-FI module 550, solenoids 410 and 420, heating elements 416 and 426, temperature sensors 418 and 428, piezoelectric vibrator 640, and pressure sensors 440, 450, 470, 480, 610, 620, and 630.

Figure 10A:
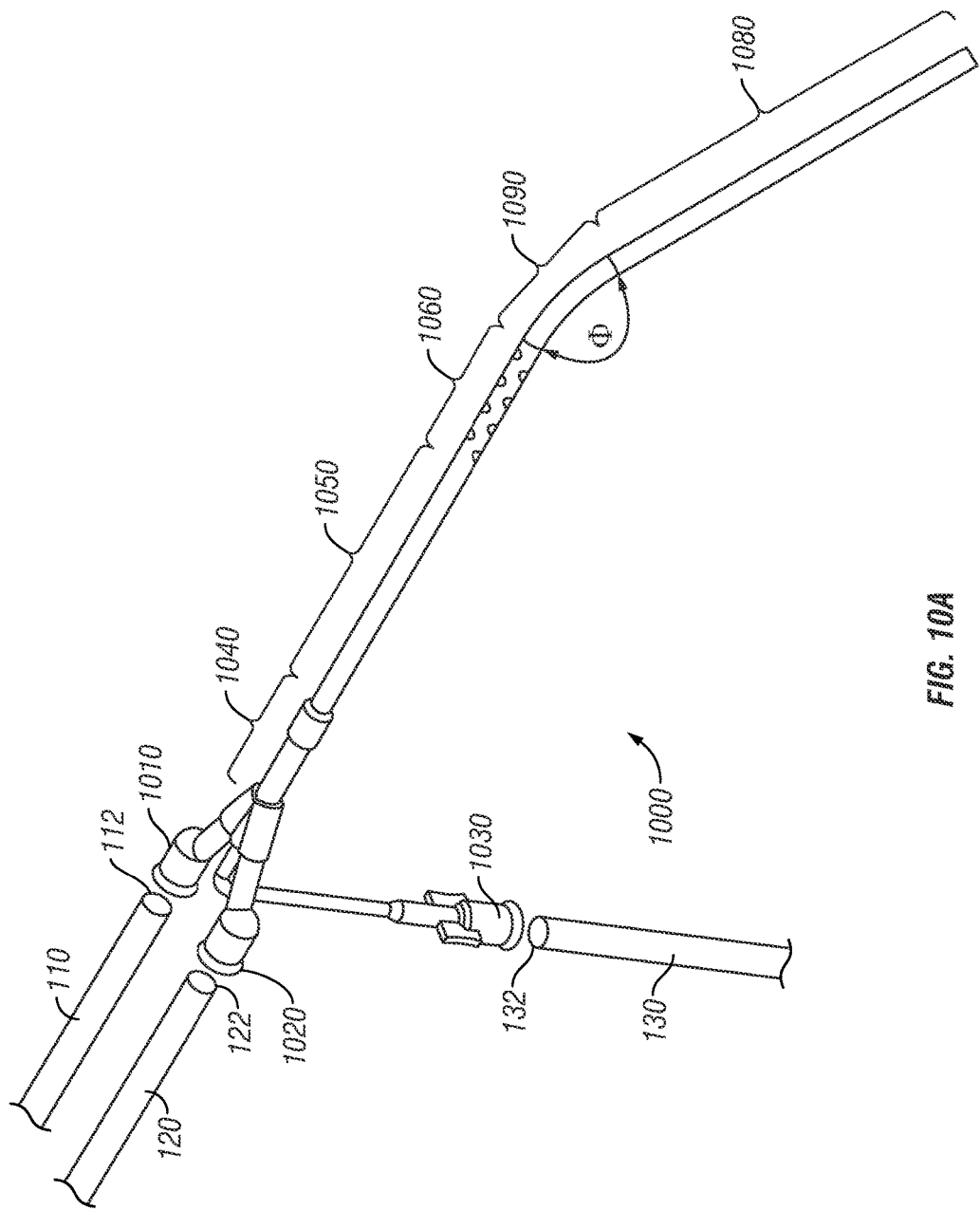
FIG. 10A is a perspective view of a third embodiment of Applicants' application apparatus.

Referring now to FIG. 10A, Applicants' application apparatus 1000 comprises an input 1010, an input 1020, and a pressurized gas input 1030. Inputs 1010, 1020, and 1030, are fluidly joined to form input assembly 1040. Tubular flow assembly 1050 fluidly interconnects with input assembly 1040.

In certain embodiments and referring to FIG. 10D, input 1010 is configured to couple with output port 950 of dispensing apparatus 900, input 1020 is configured to couple with output port 960 of dispensing apparatus 900, and input 1030 which is configured to couple to pressurized gas output port 920 of dispensing apparatus 900. Compressed gas source line 1005 provides pressurized gas to output port 920.

In other embodiments, input 1020 interconnects with end 112 of conduit 110, input 120 interconnects with conduit 120, and input 1030 interconnects with pressurized gas source conduit 130.

In use, a thrombin stream propelled by compressed gas impingement mixes with a fibrinogen stream propelled by compressed gas to form a reaction mixture. That reaction mixture is rapidly propelled through tubular flow assembly 1050 by the pressurized gas.

Turbulent mixing assembly 1060 fluidly interconnects with a distal end of assembly 1050. In fluid dynamics, turbulence is a flow regime characterized by chaotic property changes. This includes low momentum diffusion, high momentum convection, and rapid variation of pressure and velocity in space and time.

In certain embodiments, a thrombin stream and a fibrinogen stream are propelled through turbulent mixing assembly 1060 by the pressurized gas in a turbulent flow. In certain embodiments, the thrombin/fibrinogen/pressurized gas mixture flows through turbulent mixing assembly with a Reynolds number (Re) greater than 5000.

In such turbulent flow, unsteady vortices appear on many scales and interact with each other. Drag due to boundary layer skin friction increases. The structure and location of boundary layer separation often changes, sometimes resulting in a reduction of overall drag.

Figure 10B:
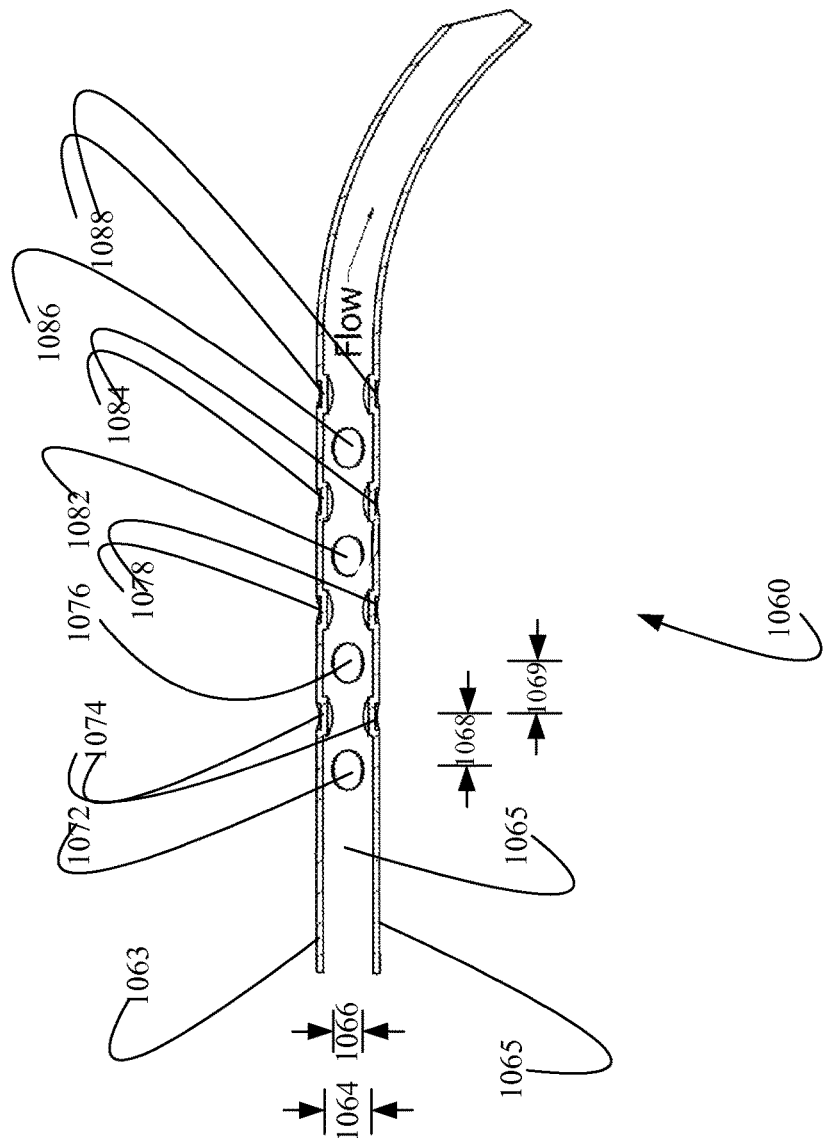
FIG. 10B illustrates a turbulent mixing assembly disposed in the application apparatus of FIG. 10A.

Turbulent mixing assembly 1060 comprises a tubular structure formed to include a plurality of inwardly-extending dimples formed therein. FIG. 10B illustrates an embodiment wherein turbulent mixing assembly 1060 is formed to include 16 dimples. These 16 dimples are formed in pairs, wherein each pair is formed in an opposing portion of the tubular structure.

For example, in the illustrated embodiment of FIG. 10B, a dimple pair 1072 is formed in a first side portion 1061 and in an opposing second side portion not shown in FIG. 10B. Similarly, dimple pairs 1076, 1082, and 1086, are formed in first side portion 1061 and in an opposing second side portion not shown in FIG. 10B.

Further in the illustrated embodiment of FIG. 10B, a pair of dimples 1074 are formed in top portion 1063 and bottom portion 1065 of turbulent mixing assembly 1060, where the top dimple is directly above the bottom dimple. Similarly, dimple pairs 1078, 1084, and 1088, are formed in top portion 1063 and bottom portion 1065 of turbulent mixing assembly 1060, where the top dimple is formed directly above the bottom dimple.

In the illustrated embodiment of FIG. 10B, a distance 1068 separates the centers of dimple pair 1072 and dimple pair 1074. In certain embodiments, distance 1068 is between about 0.2 inches and about 0.4 inches. In certain embodiments, distance 1068 is about 0.3 inches.

Further in the illustrated embodiment of FIG. 10B, a distance 1069 separates the centers of dimple pair 1074 and dimple pair 1076. In certain embodiments, distance 1069 is between about 0.2 inches and about 0.4 inches. In certain embodiments, distance 1069 is about 0.3 inches.

In certain embodiments, distance 1068 is substantially equal to distance 1069. By "substantially equal," Applicants mean plus or minus about ten percent (10%). In certain embodiments, distance 1068 is not substantially equal to distance 1069.

Portions of turbulent mixing assembly 1060 not formed to include dimple pairs comprise an inner diameter 1064. Portions of turbulent mixing assembly 1060 formed to include dimple pairs comprise a narrower inner diameter 1066. In certain embodiments, the dimension of inner diameter 1066 is between about 0.25 to about 0.75 the dimension of inner diameter 1064. In certain embodiments, the dimension of inner diameter 1066 is about 0.50 the dimension of inner diameter 1064.

The interior volume of portions of turbulent mixing assembly at a pair of inwardly extending dimples is diminished. As a result, these portions of turbulent mixing assembly 1060 comprise "contraction zones." The interior volume of portions of turbulent mixing assembly between pairs of inwardly extending dimples is increased. As a result, these portions of turbulent mixing assembly 1060 comprise "expansion zones."

In addition, the pressure exerted by the pressurized gas on the fibrinogen/thrombin reaction mixture increases in each contraction zone. On the other hand, the pressure exerted by the pressurized gas on the fibrinogen/thrombin reaction mixture decreases in each expansion zone.

The thrombin/fibrinogen reaction mixture is rapidly propelled through a series of expansion/contraction zones in turbulent mixing assembly 1060 to form Applicants' fibrin-forming foam. These alternating expansion and contraction zones result in rapid variation of pressure and velocity in space and time.

Referring once again to FIG. 10A, tubular transition zone 1090 interconnects turbulent mixing assembly 1060 and effector tube 1080. In certain embodiments, effector tube 1080 is offset from turbulent mixing assembly 1060 by an angle Φ. In certain embodiments, angle Φ is between 0 and about 60 degrees. In certain embodiments, angle Φ is about 30 degrees.

Figure 11B:
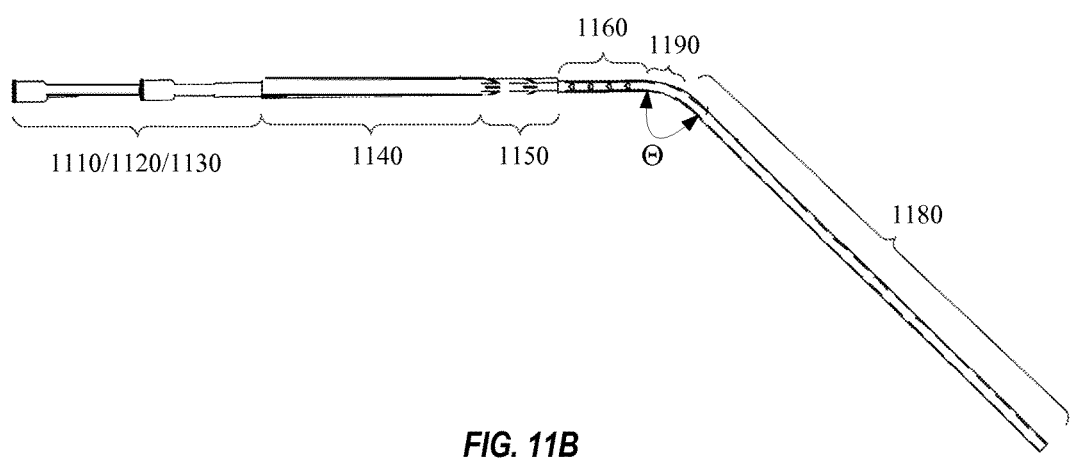
FIG. 11B is a side view of the application apparatus of FIG. 11A.

Referring now to FIGS. 11A and 11B, Applicants' application apparatus 1100 comprises input 1110, input 1120, and input 1130. Inputs 1110, 1120, and 1130, are fluidly joined to form input tubular flow assembly 1140.

In certain embodiments and referring to FIG. 11E, input 1110 is configured to couple with output port 950 of dispensing apparatus 900, input 1120 is configured to couple with output port 960 of dispensing apparatus 900, and input 1130 which is configured to couple to pressurized gas output port 920 of dispensing apparatus 900. Compressed gas source line 1105 provides pressurized gas to output port 920 of dispensing apparatus 900.

In other embodiments, input 1120 interconnects with end 112 of conduit 110, input 1120 interconnects with conduit 120, and input 1130 interconnects with pressurized gas source conduit 130. Compressed gas source line 1105 provides pressurized gas to output port 920.

A distal end of tubular flow assembly 1140 fluidly connects to a proximal end of tubular venturi assembly 1150. A distal end of venturi assembly 1050 fluidly connects to a proximal end of turbulent mixing assembly 1160. A transition zone 1190 interconnects turbulent mixing assembly 1160 and effector tube 1180. In certain embodiments, effector tube 1180 is offset from turbulent mixing assembly 1160 by an angle Θ. In certain embodiments, angle Θ is between 0 and about 60 degrees. In certain embodiments, angle Θ is about 30 degrees.

Venturi assembly 1150 comprises an outer surface 1152 and a lumen extending therethrough. In certain embodiments, venturi assembly 1150 comprises venturi assembly inner diameter. In certain embodiments, the venturi assembly inner diameter is about 0.30 inches and about 0.30 inches. In certain embodiments, the venturi assembly inner diameter is between about 0.20 inches and about 0.40 inches.

Venturi assembly 1150 is formed to include an interior lumen and a plurality of air channels formed between the outer surface and the lumen. In the illustrated embodiment of FIG. 11C, a total of 8 air channels are formed in venturi assembly 1150. Further in the illustrated embodiment of FIG. 11C, four pairs of air channels are formed in venturi assembly 1150. A first pair of air channels includes open ends 1210 and 1220 formed in outer surface 1152.

A first air channel includes a first open end 1210 formed in outer surface 1152, a second open end 1214 formed in inner surface 1154, and an aperture 1212 interconnecting first open end 1210 and second open end 1214. A second air channel includes a first open end 1220 formed in outer surface 1152, a second open end 1224 formed in inner surface 1154, and an aperture 1222 interconnecting first open end 1220 and second open end 1224.

In certain embodiments, aperture 1212 and inner surface 1154 define an angle of between about 20 degrees and about 60 degrees. In the illustrated embodiment of FIG. 11C, aperture 1212 and inner surface 1154 define an angle of about 30 degrees.

A second pair of air channels includes outer ends 1240 and 1250 formed in outer surface 1152. The second pair is formed to include inner open ends 1244 and 1254, respectively, and apertures 1242 and 1252, respectively.

Figure 11C:
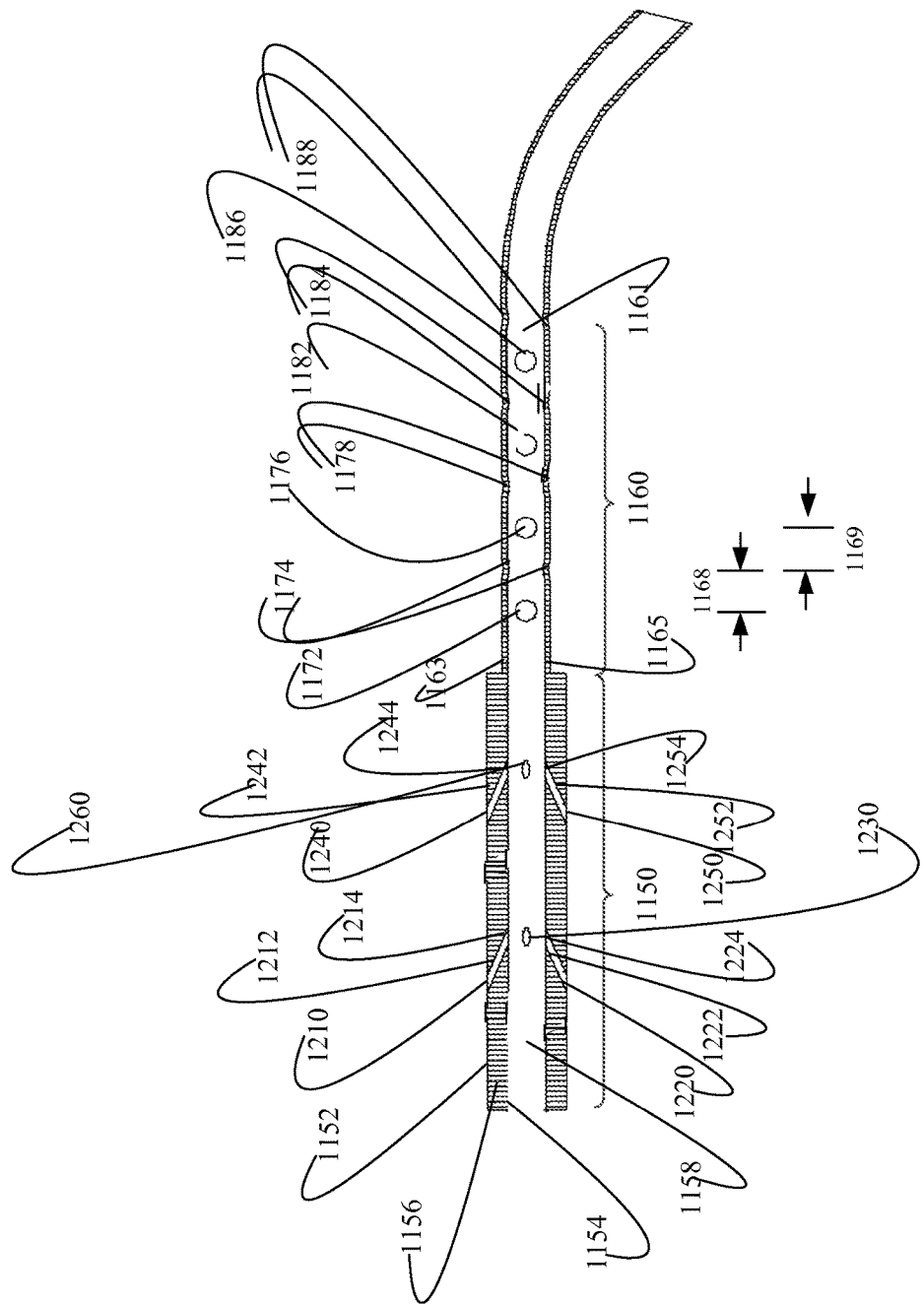
FIG. 11C illustrates a venturi assembly and a turbulent mixing assembly disposed in the application apparatus of FIG. 11A.
Figure 11D:
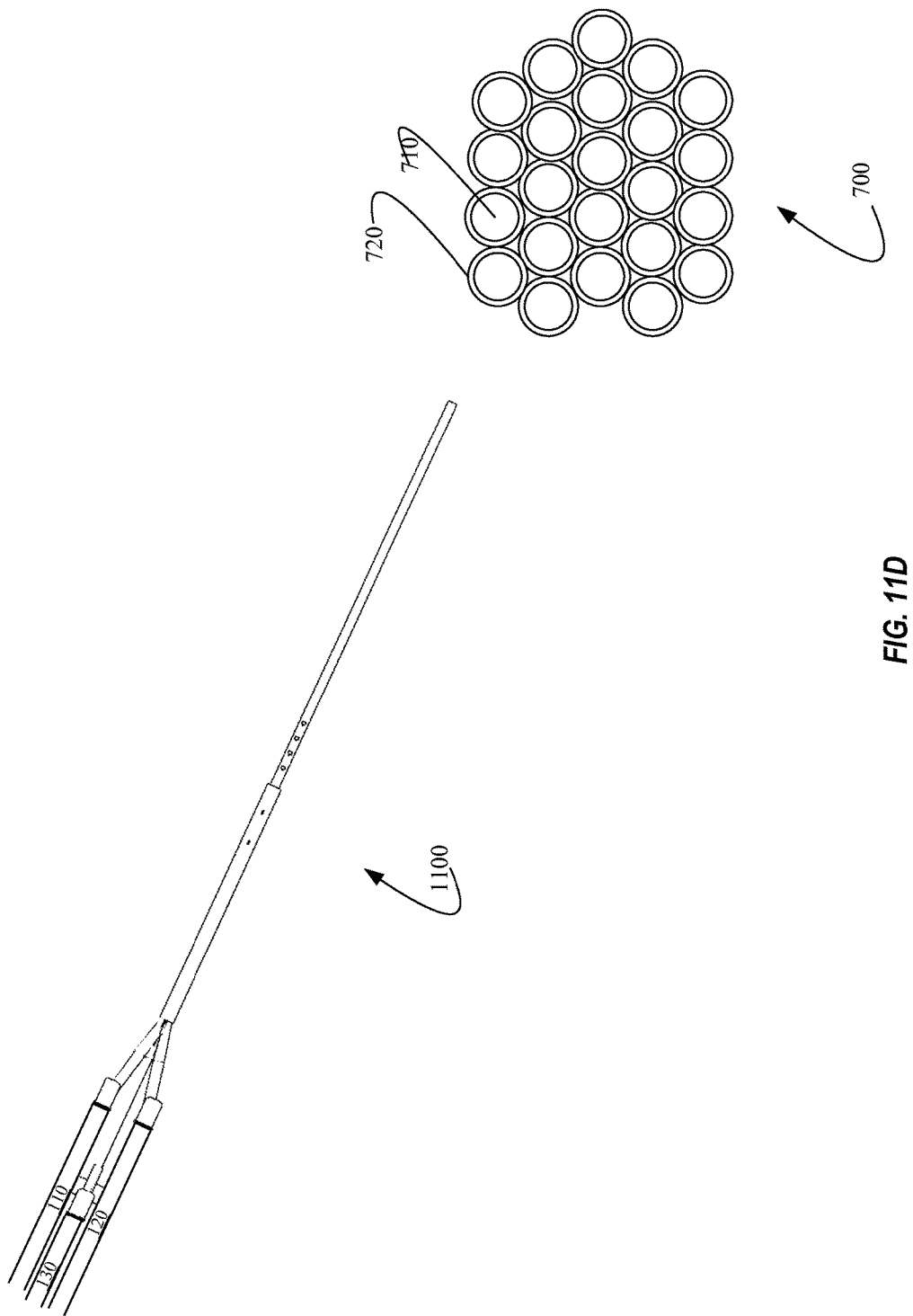
FIG. 11D illustrates formation of Applicants' fibrin-forming foam using the application apparatus of FIG. 11A.

A third pair of air channels includes open end 1230 and an opposing open end formed in a side of venturi assembly 1150 not shown in FIG. 11C. A fourth pair of air channels includes open end 1260 and an opposing open end formed in a side of venturi assembly 1150 not shown in FIG. 11C. The third and fourth pairs of air channels are formed in accord with the description of the first pair of air channels described hereinabove.

A reaction mixture of thrombin and fibrinogen is rapidly propelled through venturi assembly 1040 using the pressurized gas, ambient air is pulled into venturi assembly 1150 through the four pairs of air channels formed therein. The addition of ambient air to the thrombin/fibrinogen reaction mixture in venturi assembly 1150 causes the onset of turbulent mixing.

Turbulent mixing assembly 1160 fluidly interconnects to a distal end of venturi assembly 1150. Turbulent mixing assembly 1060 comprises a tubular structure formed to include a plurality of inwardly-extending dimples. FIG. 11C illustrates an embodiment wherein turbulent mixing assembly 1160 is formed to include 16 dimples. These 16 dimples are formed in pairs, wherein each pair is formed in an opposing portion of the tubular structure.

For example, in the illustrated embodiment of FIG. 11C, a dimple pair 1172 is formed in a first side portion 1161 and in an opposing second side portion not shown in FIG. 10B. Similarly, dimple pairs 1176, 1182, and 1186, are formed in first side portion 1161 and in an opposing second side portion not shown in FIG. 11C.

Further in the illustrated embodiment of FIG. 11C, a pair of dimples 1174 are formed in top portion 1163 and bottom portion 1165 of turbulent mixing assembly 1160, where the top dimple is directly above the bottom dimple. Similarly, dimple pairs 1178, 1184, and 1188, are formed in top portion 1163 and bottom portion 1165 of turbulent mixing assembly 1160, where the top dimple is directly above the bottom dimple.

In the illustrated embodiment of FIG. 11C, a distance 1168 separates the centers of dimple pair 1172 and dimple pair 1174. In certain embodiments, distance 1168 is between about 0.2 inches and about 0.4 inches. In certain embodiments, distance 1168 is about 0.3 inches.

Further in the illustrated embodiment of FIG. 11C, a distance 1169 separates the centers of dimple pair 1174 and dimple pair 1176. In certain embodiments, distance 1169 is between about 0.2 inches and about 0.4 inches. In certain embodiments, distance 1169 is about 0.3 inches.

In certain embodiments, distance 1168 is substantially equal to distance 1169. By "substantially equal," Applicants mean plus or minus about ten percent (10%). In certain embodiments, distance 1168 is not substantially equal to distance 1169.

Portions of turbulent mixing assembly 1160 not formed to include dimple pairs comprise an inner diameter 1164. Portions of turbulent mixing assembly 1160 formed to include dimple pairs comprise a narrower inner diameter 1166. In certain embodiments, the dimension of inner diameter 1166 is between about 0.25 to about 0.75 the dimension of inner diameter 1164. In certain embodiments, the dimension of inner diameter 1166 is about 0.50 the dimension of inner diameter 1164.

The interior volume of portions of turbulent mixing assembly at a pair of inwardly extending dimples is diminished. As a result, these portions of turbulent mixing assembly 1160 comprise "contraction zones." The interior volume of portions of turbulent mixing assembly between pairs of inwardly extending dimples is increased. As a result, these portions of turbulent mixing assembly 1160 comprise "expansion zones."

In addition, the pressure exerted by the pressurized gas on the fibrinogen/thrombin reaction mixture increases in each contraction zone. On the other hand, the pressure exerted by the pressurized gas on the fibrinogen/thrombin reaction mixture decreases in each expansion zone.

The thrombin/fibrinogen reaction mixture is rapidly propelled through a series of expansion/contraction zones in turbulent mixing assembly 1160 to form Applicants' fibrin-forming foam. These alternating expansion and contraction zones result in rapid variation of pressure and velocity in space and time.

Figure 8:
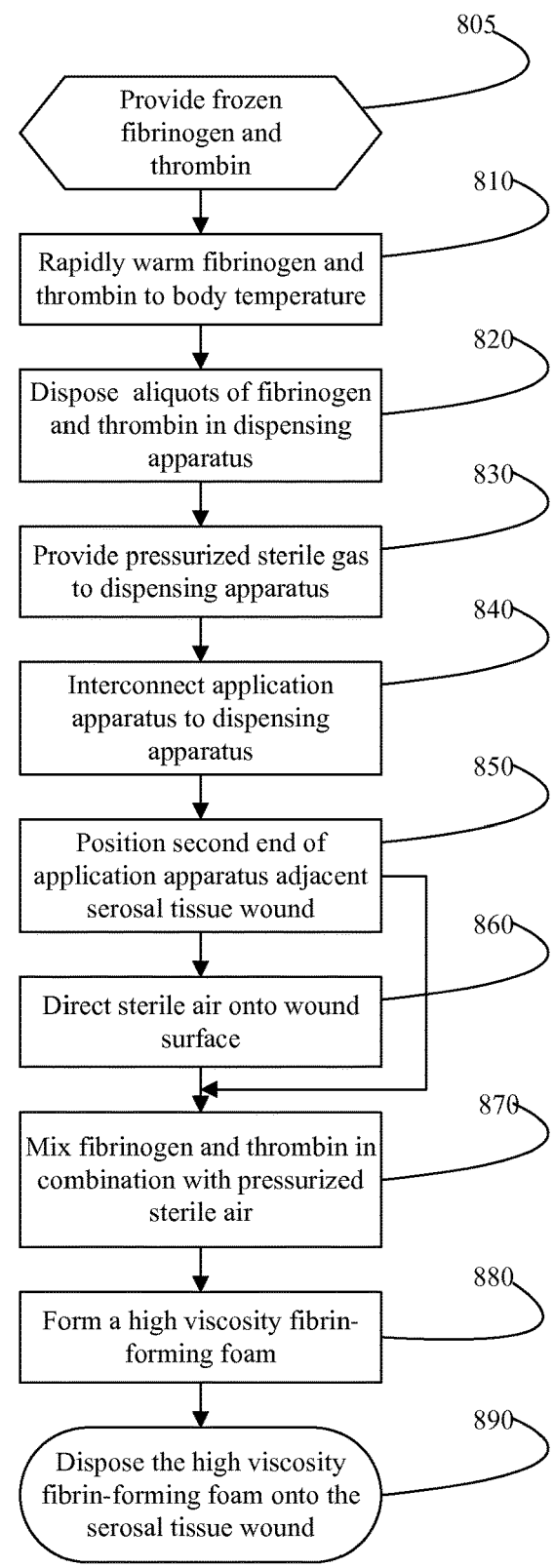
FIG. 8 summarizes Applicants' method using the various embodiments of their dispensing apparatus and application apparatus to generate Applicants' fibrin-forming foam and to dispose same onto a serosal tissue wound.

FIG. 8 is a flowchart that summarizes the steps of Applicants' method. Referring now to FIG. 8, in step 805 the method provides frozen fibrinogen and thrombin. As those skilled in the art will appreciate, fibrinogen is a plasma glycoprotein, that is converted by thrombin into fibrin in a coagulation cascade.

Fibrinogen is a 340 kDa glycoprotein comprising a hexamer comprising two sets of three different chains ($\alpha$, $\beta$, and $\gamma$), linked to each other by disulfide bonds. The N-terminal sections of these three chains contain the cysteines that participate in the cross-linking of the chains. The C-terminal parts of the $\alpha$, $\beta$ and $\gamma$ chains comprise a domain of about 225 amino-acid residues.

The conversion of fibrinogen to fibrin occurs in several steps. First, thrombin cleaves the N-terminus of the fibrinogen alpha and beta chains to fibrinopeptide A and B respectively. The resulting fibrin monomers polymerize end to end to from protofibrils, which in turn associate laterally to form fibrin fibers. In a final step, the fibrin fibers associate to form a fibrin gel.

In step 810, the frozen fibrinogen and thrombin are rapidly warmed to body temperature just prior to use. In certain embodiments, the frozen fibrinogen and thrombin are warmed from about 0° C. to about 37° C. in about 3 minutes or less. Applicants have found that a rapid thawing followed by immediate use of both the fibrinogen and the thrombin markedly increases the efficacy of their serosal tissue wound healing method. By "immediate use," Applicants mean within about 5 minutes.

In step 820, body-temperature aliquots of fibrinogen and thrombin are disposed in separate reservoirs of a dispensing apparatus. In certain embodiments, step 820 comprises disposing body-temperature aliquots of fibrinogen and thrombin into reservoirs 310 and 320, respectively, of dispensing apparatus 300 (FIGS. 3A, 3B). In certain embodiments, step 820 comprises disposing body-temperature aliquots of fibrinogen and thrombin into reservoirs 310 and 320, respectively, of dispensing apparatus 400 (FIG. 4). In certain embodiments, step 820 comprises disposing body-temperature aliquots of fibrinogen and thrombin into reservoirs 310 and 320, respectively, of sub-assembly 905 (FIG. 9C) which is disposed in dispensing apparatus 900 (FIG. 9A).

In certain embodiments, step 820 comprises disposing body-temperature aliquots of fibrinogen and thrombin into reservoirs 310 and 320, respectively, of dispensing apparatus 400. In these embodiments, steps 810 and 820 are performed in reverse order. Frozen aliquots of fibrinogen and thrombin are disposed in reservoirs 310 and 320, respectively, of dispensing apparatus 400. Controller 430 then activates heating elements 416 and 426 to rapidly warm the frozen aliquots of fibrinogen and thrombin to about to 37° C. Controller 430 continuously monitors temperature data from temperature sensors 418 and 428, as adjusts the current levels provided to heating elements 416 and 426 to rapidly warm the aliquots of fibrinogen and thrombin to body temperature without overshooting the target temperature of about 37° C. In certain embodiments, controller 430 causes a visual indicator, such as an LED display, to continuously display the real-time temperatures of the contents of reservoirs 310 and 320. In certain embodiments, controller 430 causes an auditory alert to indicate fibrinogen and thrombin temperatures of about 37° C.

In certain embodiments, in step 830 a source of pressurized, sterile gas is interconnected to valve 350 (FIGS. 3A, 3B, 4) in dispensing apparatus 300/400 (FIGS. 3A, 3B, 4). In certain embodiments, that pressurized gas comprises sterile air. In certain embodiments, that pressurized gas comprises 100 percent sterile oxygen.

in certain embodiments, in step 830 a source of pressurized, sterile gas is interconnected to input port 970 (FIG. 9B) in dispensing apparatus 900 (FIG. 9A). In certain embodiments, that pressurized gas comprises sterile air. In certain embodiments, that pressurized gas comprises 100 percent sterile oxygen.

In certain embodiments, in step 830 a source of pressurized, sterile gas is interconnected to input port 1030 (FIG. 10A) in application apparatus 1000 (FIG. 10A). In certain embodiments and as shown in FIG. 10D, input port 1030 is coupled to pressurized gas output port 920 of dispensing apparatus 900. In certain embodiments, that pressurized gas comprises sterile air. In certain embodiments, that pressurized gas comprises 100 percent sterile oxygen. In certain embodiments, step 830 further comprises setting a gas pressure to input port 1030 to between about 35 psi to about 65 psi. In certain embodiments, further comprises setting a gas pressure to input port 1030 to at least 50 psi or greater.

In certain embodiments, in step 830 a source of pressurized, sterile gas is interconnected to input port 1130 (FIG. 11A) in application apparatus 1100 (FIG. 11A). In certain embodiments and as shown in FIG. 11E, input port 1130 is coupled to pressurized gas output port 920 of dispensing apparatus 900. In certain embodiments, that pressurized gas comprises sterile air. In certain embodiments, that pressurized gas comprises 100 percent sterile oxygen. In certain embodiments, step 830 further comprises setting a gas pressure to input port 1130 to between about 35 psi to about 65 psi. In certain embodiments, further comprises setting a gas pressure to input port 1130 to at least 50 psi or greater.

In certain embodiments, step 830 further comprises setting an outlet pressure on valve 350 to between about 35 psi to about 65 psi. In certain embodiments, further comprises setting an outlet pressure on valve 350 to at least 50 psi or greater.

In certain embodiments, in step 830 controller 430 monitors an input pressure to valve 350 using pressure sensor 440. In certain embodiments, controller 430 causes a visual indicator, such as an LED display, to continuously display the real-time pressure measured by pressure sensor 440. In certain embodiments, controller 430 causes an auditory alert to indicate that the real-time pressure measured by pressure sensor 440 is less than about 35 psi.

In step 840, an application apparatus, such as application apparatus 100, 600, 1000, or 1100, is interconnected with the dispensing apparatus of step 820, such as dispensing apparatus 300, 400, or 900.

In step 850, a distal end of the application apparatus of step 840 is positioned adjacent a serosal tissue wound surface. In certain embodiments, step 850 comprises positioning end 104 of application apparatus 100 adjacent a serosal tissue wound surface. In certain embodiments, step 850 comprises positioning end 604 of application apparatus 600 adjacent a serosal tissue wound surface. In certain embodiments, step 850 comprises positioning a distal end of application apparatus 1000 adjacent a serosal tissue would surface. In certain embodiments, step 850 comprises positioning a distal end of application apparatus 1100 adjacent a serosal tissue would surface.

In certain embodiments, the serosal tissue wound surface of step 850 comprises tissue comprising a lung. In certain embodiments, the serosal tissue wound surface of step 850 comprises lung tissue following pulmonary surgery.

In certain embodiments, the serosal tissue wound surface of step 850 comprises tissue comprising an esophagus. In certain embodiments, the serosal tissue wound surface of step 850 comprises tissue comprising a stomach. In certain embodiments, the serosal tissue wound surface of step 850 comprises tissue comprising an intestine, either large or small. In certain embodiments, the serosal tissue wound surface of step 850 comprises tissue comprising a liver. In certain embodiments, the serosal tissue wound surface of step 850 comprises tissue comprising a pancreas. In certain embodiments, the serosal tissue wound surface of step 850 comprises tissue comprising a spleen.

In certain embodiments, Applicants method transitions from step 850 to step 860 wherein the pressurized sterile gas of step 830 is directed onto the serosal tissue wound surface of step 850 to cleanse that wound surface. Applicants' method transitions from step 860 to step 870.

In certain embodiments, Applicants' method transitions from step 850 to step 870 wherein the method mixes body-temperature fibrinogen and thrombin using one or more pressurized gases as a carrier.

In certain embodiments, step 870 includes spray mixing, and/or impingement mixing, fibrinogen and thrombin from apertures using application apparatus 100. In these embodiments, step 870 causes the pressurized sterile gas of step 830 to flow outwardly from aperture 134 in catheter 130 disposed in either application apparatus 100 or application apparatus 600.

In certain embodiments, step 870 includes impingement mixing a fibrinogen streams and a thrombin stream within application apparatus 1000. In these embodiments, step 870 includes mixing body-temperature fibrinogen and thrombin in application device 1000 in the presence of one or more pressurized gasses, forming a fibrinogen/thrombin reaction mixture in flow assembly 1050 and turbulently mixing that fibrinogen/thrombin reaction mixture in turbulent mixing assembly 1060.

In certain embodiments, step 870 includes impingement mixing a fibrinogen streams and a thrombin stream within application apparatus 1100. In these embodiments, step 870 includes mixing body-temperature fibrinogen and thrombin in application device 1100 in the presence of one or more pressurized gasses, forming a fibrinogen/thrombin reaction mixture in flow assembly 1140, initiating turbulent mixing of that fibrinogen/thrombin reaction mixture in venturi assembly 1150, and increasing the turbulent mixing of the fibrinogen/thrombin reaction mixture in turbulent mixing assembly 1160.

In embodiments, wherein dispensing apparatus 300 is utilized, step 870 comprises moving activation member 340 inwardly toward reservoirs 310 and 320 to cause pistons 312 and 322, respectively, to push body-temperature fibrinogen and thrombin, respectively, outwardly from reservoirs 310 and 320, respectively, though outlet ports 316 and 326, respectively, through conduits 318 and 328, respectively, through catheters 110 and 120, respectively, and finally outwardly from apertures 114 and 124. Valve 350 is synchronously opened to cause the pressurized sterile gas to flow through conduit 338, through catheter 130, and outwardly from aperture 134.

In embodiments wherein dispensing apparatus 400 is utilized, step 870 comprises controller 430 causing solenoids 410 and 420 to move armatures 412 and 422, respectively, inwardly toward reservoirs 310 and 320 to cause pistons 312 and 322, respectively, to push body-temperature fibrinogen and thrombin, respectively, outwardly from reservoirs 310 and 320, respectively, though outlet ports 316 and 318, respectively, through conduits 318 and 328, respectively, through catheters 110 and 120, respectively, and finally outwardly from apertures 114 and 124. Controller 430 opens valve 350 thereby causing the pressurized sterile gas to flow through conduit 338, through catheter 130, and outwardly from aperture 134. In certain embodiments, controller 430 continuously monitors the pressure in conduit 338 using pressure sensor 450. In certain embodiments, controller 430 continuously monitors the pressure at end 604 of application apparatus 600 using pressure sensors 610, 620, and 630.

In embodiments wherein dispensing apparatus 900 (FIGS. 9A, 9) is utilized, step 870 comprises depressing activation button 990 thereby causing pneumatic plunger 940 to rapidly move activation member 340 forward thereby causing pistons 312 and 322 to rapidly expel thrombin and fibrinogen outwardly from reservoirs 310 and 320 of sub-assembly 905 into an application device 100, 600, 1000, or 1100.

Figure 7:
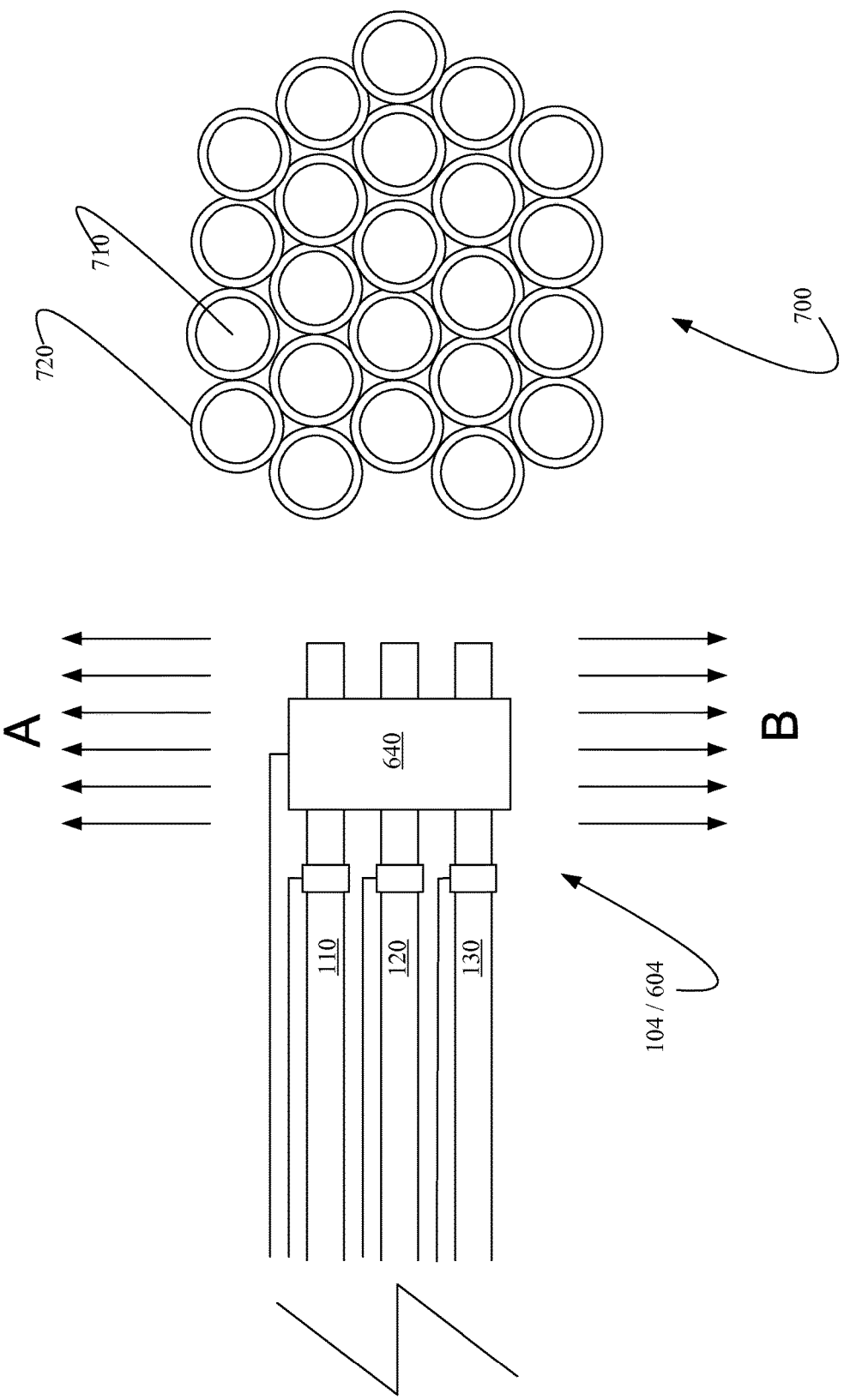
FIG. 7 graphically illustrates one embodiment of formation of Applicants' fibrin-forming foam.

In atop 880, a fibrinogen/thrombin reaction mixture, in combination with one or more pressurized gases, forms a fibrin-forming cellular reaction mixture 700, i.e. a foam. Referring now to FIG. 7, in certain embodiments the fibrin-forming foam 700 comprises a plurality of cell walls 720, wherein each cell wall define an interior space comprising the sterile gas.

In certain embodiments, agitation/vibration of the distal end of Applicants' application apparatus 104/604 along the directions of arrows A and arrows B, e.g. orthogonal to the sprayed fibrinogen and thrombin, lowers the bulk viscosity of the fibrin-forming cellular reaction mixture 700. This being the case, fibrin-forming foam 700 comprises a non-Newtonian fluid, i.e. a sheer-thinning fluid.

Figure 10C:
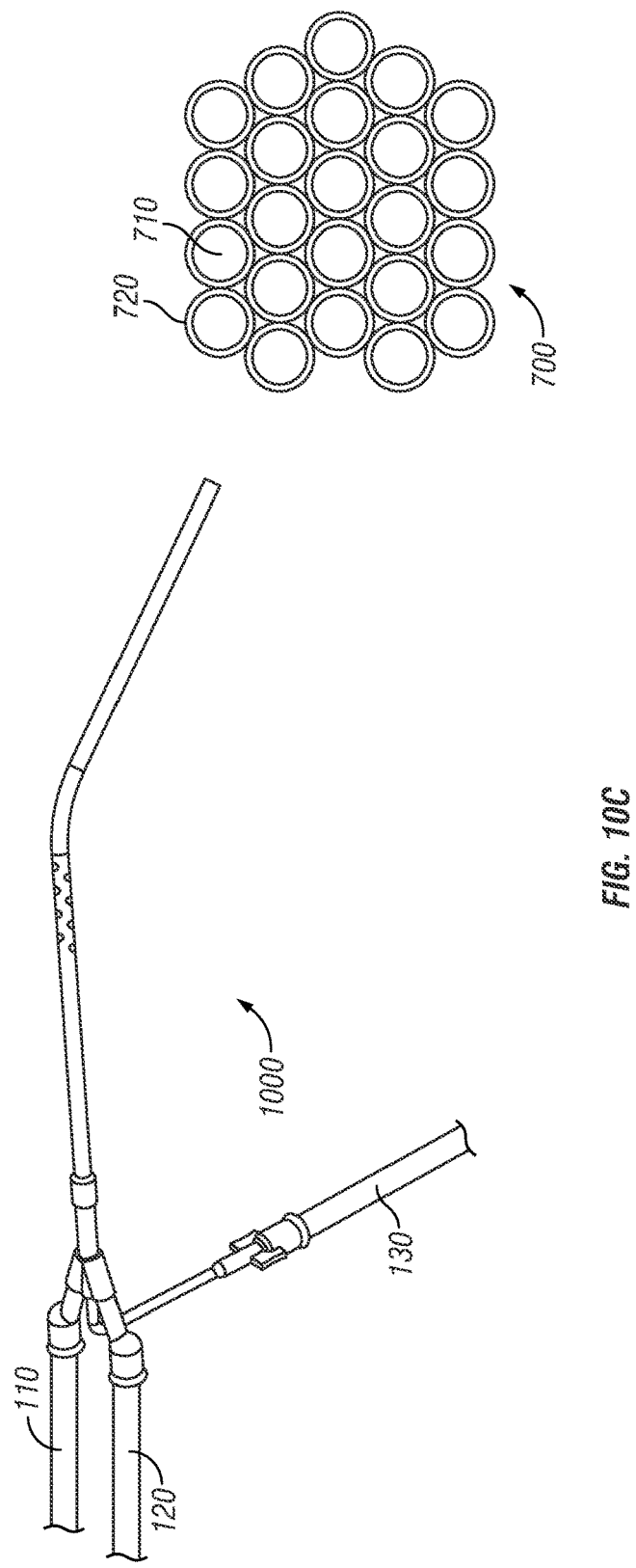
FIG. 10C illustrates formation of Applicants' fibrin-forming foam using the application apparatus of FIG. 10A.

Referring now to FIGS. 10A and 10C, in certain embodiments, rapid movement of the fibrinogen/thrombin reaction mixture through delivery apparatus 1000 comprising a turbulent mixing assembly 1060 using a pressurized gas forms Applicants' fibrin-forming cellular reaction mixture 700. In certain embodiments, fibrin-forming foam 700 comprises a non-Newtonian fluid, i.e. a sheer-thinning fluid.

Referring now to FIGS. 11A, 11B, and. 11D, in certain embodiments, using delivery apparatus 1100 and a pressurized gas to rapidly propel the fibrinogen/thrombin reaction mixture through venturi assembly 1150 and then through turbulent mixing assembly 1160 forms Applicants' fibrin-forming foam 700. In certain embodiments, fibrin-forming foam 700 comprises a non-Newtonian fluid, i.e. a sheer-thinning fluid.

Shear thinning is an effect where a fluid's viscosity—the measure of a fluid's resistance to flow—decreases with an increasing rate of shear stress. Another name for a shear thinning fluid is a pseudoplastic.

The pseudoplasticity of fibrin-forming foam 700 causes that composition to undergo a change in viscosity due to the sheering stress resulting from agitation/vibration of distal ends of application apparatus 100/600. These sheering forces change the viscosity of the fibrin-forming foam 700 from a honey-like consistency to a low viscosity fluid which flows like water. When fibrin-forming foam 700 leaves the vicinity of Applicants' application apparatus, and is spread onto a serosal tissue wound surface, the sheering forces slowly relax. The internal structure of Applicants' fibrin-forming foam 700 can sustain the stress forces for a short period of time referred to as a relaxation time.

As those skilled in the art will appreciate, a serosal tissue wound site does not comprise a smooth, continuous surface. Rather, such a serosal tissue wound site can comprise a three-dimensional structure comprising many irregular surfaces. During the relaxation period, Applicants' fibrin-forming foam 700 can cover and penetrate such a variety of irregular surfaces, tissue boundaries, and the like.

Once applied to a serosal tissue wound site, and after the relaxation period has expired, Applicants' fibrin-forming foam 700 regains a high viscosity consistency, and tenaciously adheres to all areas of the serosal tissue wound surface and edges.

Applicants have found that a serosal tissue wound site treated with Applicants' fibrin-forming foam 700 heals much faster than either an untreated serosal tissue wound site, or a serosal tissue wound site treated with prior art techniques and compositions. Applicants have further discovered that such enhanced healing of lung tissues results in a dramatic decrease in air leakage after surgery.

Johnson & Johnson sells a product in commerce under the trade name FIBRIN SEALANT (HUMAN) EVICEL ("Evicel"). The Evicel product includes frozen vials of BAC2 and Thrombin.

A package insert for Evicel recites Johnson & Johnson usage guidelines (the "J&J Guidelines"). Under the J&J Guidelines, use of Evicel is strictly limited to "topical use." The J&J Guidelines describe the use of Evicel as an adjunct to hemostasis, when control of bleeding by standard surgical techniques (such as suture, ligature or cautery) is ineffective or impractical." (EVICEL package insert at Section 1). In marked contrast, Applicants' apparatus and method is used to facilitate rapid healing of serosal tissue wounds, and in particular, healing of lung tissues after surgery.

The J&J Guidelines recommend thawing vials of BAC2 and Thrombin in one of three ways: (i) using a refrigerator at 2° C. to 8° C. for 1 day, (ii) room temperature of 20° C. to 25° C. for 1 hour, or (iii) active heating at 37° C. for 10 minutes. After thawing, John & Johnson guidelines permit storage of the thawed components for up to 30 days with refrigeration or 24 hours at room temperature.

Once again in marked contrast to the J&J Guidelines prior art, Applicants' method warms the frozen fibrinogen and thrombin 0° C. to 37° C. in about 3 minutes or less. Applicants have found that a rapid thawing followed by immediate use of both the fibrinogen and the thrombin markedly increases the efficacy of their serosal tissue wound healing method. By "immediate use," Applicants mean within about 5 minutes after reaching 37° C.

The J&J guidelines recommend application of Evicel by dripping, i.e. "apply individual drops to the surface area to be treated." Furthermore, the J&J Guidelines require the operator to "allow the drops to separate from each other and from the tip of the applicator." Needless to say, the J&J Guidelines do not teach or suggest forming a fibrin-forming foam.

Alternatively, the J&J Guidelines permit application of Evicel by spraying using "a pressure regulator capable of delivering between 15-25 psi of pressure." Furthermore, the J&J Guidelines require utilization of "spray pressure that is within the recommended guidelines of the device manufacturer, e.g. an air pressure of 15-25 psi measured by airflow." Significantly, in Section 5 entitled "WARNINGS AND PRECUATIONS" the J&J guidelines expressly provide "air or gas embolism has occurred with the use of spray devices employing a pressure regulator to administer EVICEL. This event appears to be related to the use of the spray device at higher than recommended pressures." These WARNING AND PRECAUTIONS further provide "avoid using pressure above 20-25 psi." The J&J Guidelines do not anywhere recommend agitation of the distal ends of the spray device Applicants have found that using the J&J Guideline pressures of 20-25 psi that the spray pattern produced comprises a plurality of individual, droplets, rather than an aerosolized mist formed using higher pressures.

Applicants' method and apparatus produces neither a plurality of individual droplets, nor an aerosolized mist. Rather in certain embodiments, Applicants' method utilizes a gas pressure of at least 50 psi or greater to spray mix or impingement mix streams of fibrinogen and thrombin to form a high viscosity, fibrin-foaming foam. By "high viscosity," Applicants mean that if Applicants fibrin-forming foam is applied to a vertical surface, that foam will attach to, and remain in place, on that vertical surface. Applicants have found that application of fibrin-forming foam 700 to serosal wound tissues greatly enhances aerostasis in pulmonary surgery.

The following Examples are presented to further illustrate to persons skilled in the art how to make and use the invention. These examples are not intended as a limitation, however, upon the scope of the invention.

Example 1

EVICEL Product Using J&J Guidelines

Applicants have found that using the Evicel product in combination with the J&J Guidelines during lung tissue surgery, patients inevitably experience about a 25% air leakage rate immediately after surgery. As described hereinabove, air leakage leads in increased morbidity and mortality. Those of ordinary skill in the surgical arts will appreciate that increased air leakage necessarily leads to increased morbidity and mortality.

Example 2

Use of Applicants' Apparatus with a Slow Thaw and without Agitation

Using Applicants' apparatus and a measured airflow of about 50 psi, but without agitation of the distal ends of the application apparatus, did not produce a fibrin-forming foam 700. Using this technique during lung tissue surgery, 200 patients experienced about a 2.5% air leakage rate immediately after surgery.

Example 3

Use of Applicants' Apparatus and Method Applying Cellular Fibrin-Forming Foam

Using Applicants' apparatus and a measured airflow of about 50 psi in combination with agitation of the distal ends of the spray apparatus did produce fibrin-forming foam 700, wherein that foam comprised a true Non-Newtonian fluid. Using Applicants' method and apparatus during lung tissue surgery, 200 patients experienced about a 1.5% air leakage rate immediately after surgery.

While the preferred embodiments of the present invention have been illustrated in detail, it should be apparent that modifications and adaptations to those embodiments may occur to one skilled in the art without departing from the scope of the present invention as set forth herein.

We claim:

1. A method for preventing air leaks from a serosal tissue wound, comprising:
   providing a device comprising a dispensing apparatus and a delivery apparatus in fluid communication with said dispensing apparatus;
   rapidly warming frozen aliquots of fibrinogen and thrombin from about 0° C. to about 37° C. in about 3 minutes or less;
   after fibrinogen aliquots and thrombin aliquots are rapidly warmed to about 37° C., the fibrinogen and thrombin aliquots are provided within about 5 minutes from said dispensing apparatus to said delivery apparatus;
   mixing a fibrinogen stream and a thrombin stream in a pressurized gas stream, said pressurized gas stream having a pressure of 50 psi or greater;
   generating a fibrin-forming foam; and
   directing said fibrin-forming foam onto said serosal tissue wound.

2. The method of claim 1, wherein said pressurized gas stream is integral with said dispensing apparatus.

3. The method of claim 2, wherein said dispensing apparatus comprises a pneumatic plunger.

4. The method of claim 2, wherein said dispensing apparatus comprises a pressure regulator in fluid communication with said pressurized gas stream.

5. The method of claim 1, further comprising:
   coupling a fibrinogen input of said delivery apparatus to a fibrinogen output of said dispensing apparatus;
   coupling a thrombin input of said delivery apparatus to a thrombin output of said dispensing apparatus; and
   coupling a pressurized gas input of said delivery apparatus to a pressurized gas output of said dispensing apparatus.

6. The method of claim 1, wherein said delivery apparatus comprises a turbulent mixing assembly, said method further comprising generating in said turbulent mixing assembly a flow of a thrombin/fibrinogen reaction mixture having a Reynolds number greater than 5000.

7. The method of claim 6, wherein said turbulent mixing assembly is formed to include a plurality of inwardly extending dimples.

8. The method of claim 7, wherein said plurality of inwardly extending dimples are formed in opposing pairs on said turbulent mixing assembly.

9. The method of claim 1, wherein:
   said delivery apparatus further comprises a venturi assembly in fluid communication with a turbulent mixing assembly;
   said venturi assembly comprises a tubular structure having an outer surface and a lumen extending therethrough;
   said venturi assembly is formed to include a plurality of air passages extending from said outer surface to said lumen; and
   said method further comprises initiating turbulent mixing of said thrombin stream and said fibrinogen stream in said venturi assembly.

10. The method of claim 9, wherein said plurality of air passages are formed in opposing pairs in said venturi assembly.

* * * * *